(12) United States Patent
Nettekoven et al.

(10) Patent No.: US 7,612,076 B2
(45) Date of Patent: Nov. 3, 2009

(54) PIPERAZINYL-PYRIDINE DERIVATIVES

(75) Inventors: Matthias Heinrich Nettekoven, Grenzach-Wyhlen (DE); Olivier Roche, Folgensbourg (FR); Rosa Maria Rodriguez-Sarmiento, Basel (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 12/246,523

(22) Filed: Oct. 7, 2008

(65) Prior Publication Data

US 2009/0042903 A1 Feb. 12, 2009

Related U.S. Application Data

(62) Division of application No. 11/301,052, filed on Dec. 12, 2005, now Pat. No. 7,456,175.

(30) Foreign Application Priority Data

Dec. 16, 2004 (EP) .................................. 04106620

(51) Int. Cl.
*A61K 31/496* (2006.01)
*C07D 213/72* (2006.01)
*C07D 213/74* (2006.01)

(52) U.S. Cl. .................................. 514/253.01; 544/360

(58) Field of Classification Search .................. None
See application file for complete search history.

(56) References Cited

FOREIGN PATENT DOCUMENTS

WO 2004/089905 A1 * 10/2004

OTHER PUBLICATIONS

Burks 1994 in Johnson L.R. ed., Physiology of the Gastrointestinal Tract, Raven Press, NY, pp. 211-242.
Leurs et al., Br J. Pharmacol. 1991, 102, pp. 179-185.
Raithel et al., Int. Arch. Allergy Immunol. 1995, 108, 127-133.
Panula et al., Proc. Natl. Acad. Sci. USA 1984, 81, 2572-2576.
Inagaki et al., J. Comp. Neurol 1988, 273, 283-300.
Arrang et al., Nature 1983, 302, 832-837.
Arrang et al., Neuroscience 1987, 23, 149-157.
Clapham & Kilpatrik, Br. J. Pharmacol. 1982, 107, 919-923.
Blandina et al. in The Histamine H3 Receptor (Leurs RL and Timmermann H eds, 1998, pp. 27-40, Elsevier, Amsterdam, The Netherlands.
Masaki et al; Endocrinol. 2003, 144, 2741-2748.
Hancock et al., European J. of Pharmacol. 2004, 487, 183-197.
Timmermann, J. Med. Chem. 1990, 33, 4-11.

* cited by examiner

*Primary Examiner*—Emily Bernhardt
(74) *Attorney, Agent, or Firm*—George W. Johnston; Dennis P. Tramaloni; Samuel H. Megerditchian

(57) ABSTRACT

The present invention relates to compounds of formula I

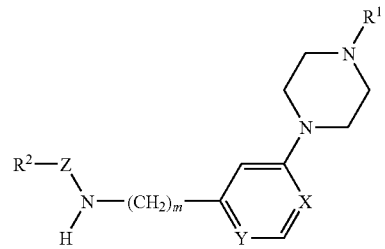

wherein $R^1$, $R^2$, X, Y, Z and m are as defined in the description and claims, and pharmaceutically acceptable salts thereof as well as to pharmaceutical composition comprising these compounds and to methods for their preparation. The compounds are useful for the treatment and/or prevention of diseases which are associated with the modulation of H3 receptors.

21 Claims, No Drawings

PIPERAZINYL-PYRIDINE DERIVATIVES

PRIORITY TO RELATED APPLICATIONS

This application is a division of U.S. application Ser. No. 11/301,052, filed Dec. 12, 2005, now allowed, which claims the benefit of priority to European Application No. 04106620.0 filed Dec. 16, 2004, which is hereby incorporated by reference in its entirety.

FIELD OF THE INVENTION

The present invention is directed to, for example, novel pyridine derivatives, their manufacture, pharmaceutical compositions containing them and their use as medicaments. The active compounds of the present invention are useful in treating obesity and other disorders.

In particular, the present invention relates to compounds of the general formula

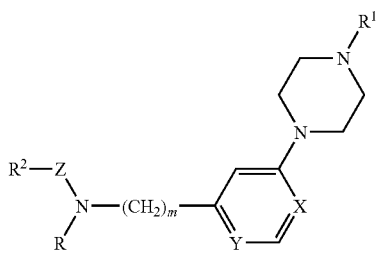

I and pharmaceutically acceptable salts thereof.

The compounds of formula I are antagonists and/or inverse agonists at the histamine 3 receptor (H3 receptor).

All documents cited or relied upon below are expressly incorporated herein by reference.

BACKGROUND OF THE INVENTION

Histamine (2-(4-imidazolyl)ethylamine) is one of the aminergic neurotransmitters which is widely distributed throughout the body, e.g. the gastrointestinal tract (Burks 1994 in Johnson L. R. ed., Physiology of the Gastrointestinal Tract, Raven Press, NY, pp. 211-242). Histamine regulates a variety of digestive pathophysiological events like gastric acid secretion, intestinal motility (Leurs et al., Br J. Pharmacol. 1991, 102, pp 179-185), vasomotor responses, intestinal inflammatory responses and allergic reactions (Raithel et al., Int. Arch. Allergy Immunol. 1995, 108, 127-133). In the mammalian brain, histamine is synthesized in histaminergic cell bodies which are found centrally in the tuberomammillary nucleus of the posterior basal hypothalamus. From there, the cell bodies project to various brain regions (Panula et al., Proc. Natl. Acad. Sci. USA 1984, 81, 2572-2576; Inagaki et al., J. Comp. Neurol 1988, 273, 283-300).

According to current knowledge, histamine mediates all its actions in both the central nervous system (CNS) and in the periphery through four distinct histamine receptors, the histamine H1, H2, H3 and H4 receptors.

H3 receptors are predominantly localized in the CNS. As an autoreceptor, H3 receptors constitutively inhibit the synthesis and secretion of histamine from histaminergic neurons (Arrang et al., Nature 1983, 302, 832-837; Arrang et al., Neuroscience 1987, 23, 149-157). As heteroreceptors, H3 receptors also modulate the release of other neurotransmitters such as acetylcholine, dopamine, serotonin and norepinephrine among others in both the central nervous system and in peripheral organs, such as lungs, cardiovascular system and gastrointestinal tract (Clapham & Kilpatrik, Br. J. Pharmacol. 1982, 107, 919-923; Blandina et al. in The Histamine H3 Receptor (Leurs R L and Timmermann H eds, 1998, pp 27-40, Elsevier, Amsterdam, The Netherlands). H3 receptors are constitutively active, meaning that even without exogenous histamine, the receptor is tonically activated. In the case of an inhibitory receptor such as the H3 receptor, this inherent activity causes tonic inhibition of neurotransmitter release. Therefore it may be important that a H3R antagonist would also have inverse agonist activity to both block exogenous histamine effects and to shift the receptor from its constitutively active (inhibitory) form to a neutral state.

The wide distribution of H3 receptors in the mammalian CNS indicates the physiological role of this receptor. Therefore the therapeutic potential as a novel drug development target in various indications has been proposed.

The administration of H3R ligands—as antagonists, inverse agonists, agonists or partial agonists—may influence the histamine levels or the secretion of neurotransmitters in the brain and the periphery and thus may be useful in the treatment of several disorders. Such disorders include obesity, (Masaki et al; Endocrinol. 2003, 144, 2741-2748; Hancock et al., European J. of Pharmacol. 2004, 487, 183-197), cardiovascular disorders such as acute myocardial infarction, dementia and cognitive disorders such as attention deficit hyperactivity disorder (ADHD) and Alzheimer's disease, neurological disorders such as schizophrenia, depression, epilepsy, Parkinson's disease, and seizures or convulsions, sleep disorders, narcolepsy, pain, gastrointestinal disorders, vestibular dysfunction such as Morbus Meniere, drug abuse and motion sickness (Timmermann, J. Med. Chem. 1990, 33, 4-11).

SUMMARY OF THE INVENTION

In one embodiment of the present invention, provided is a compound of the formula I:

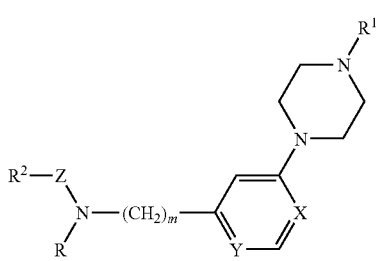

I wherein:
R is hydrogen or lower alkyl;
$R^1$ is selected from the group consisting of hydrogen, lower alkyl, $C_3$-$C_7$-alkenyl, $C_3$-$C_7$-alkinyl, lower halogenalkyl, lower hydroxyalkyl, lower alkoxyalkyl, $C_3$-$C_7$-cycloalkyl and lower $C_3$-$C_7$-cycloalkylalkyl;
X is N and Y is C, or
Y is N and X is C;
m is 0 or 1;
Z is C(O) or $SO_2$;
$R^2$ is selected from the group consisting of lower alkyl, $C_3$-$C_7$-alkenyl, $C_3$-$C_7$-alkinyl, lower halogenalkyl, lower hydroxyalkyl, lower alkoxyalkyl,
$C_3$-$C_7$-cycloalkyl or $C_3$-$C_7$-cycloalkyl substituted by phenyl or lower alkyl, lower $C_3$-$C_7$-cycloalkylalkyl,
unsubstituted phenyl or phenyl mono- or disubstituted by lower alkyl, lower alkoxy, halogen or lower halogenalkyl, lower phenylalkyl wherein the phenyl ring is unsubstituted or mono- or disubstituted by lower alkyl, lower alkoxy, halogen or lower halogenalkyl, unsubstituted pyridyl or pyridyl mono- or disubstituted by lower alkyl, lower alkoxy, halogen or lower halogenalkyl, and

—NR³R⁴, or, in case Z is C(O), R² can also be lower alkoxy or lower alkoxyalkoxy;

R³ is hydrogen or lower alkyl;

R⁴ is selected from the group consisting of lower alkyl, $C_3$-$C_7$-alkenyl, $C_3$-$C_7$-alkinyl, lower alkoxyalkyl, $C_3$-$C_7$-cycloalkyl, $C_3$-$C_7$-cycloalkyl substituted by phenyl, lower $C_3$-$C_7$-cycloalkylalkyl, unsubstituted phenyl or phenyl mono- or disubstituted by lower alkyl, lower alkoxy, halogen or lower halogenalkyl, or lower phenylalkyl wherein phenyl is unsubstituted or mono- or disubstituted by lower alkyl, lower alkoxy, halogen or lower halogenalkyl; or R³ and R⁴ together with the nitrogen atom to which they are attached form a 4-, 5-, 6- or 7-membered heterocyclic ring optionally containing a further heteroatom selected from nitrogen, oxygen or sulfur, said heterocyclic ring being unsubstituted or substituted by one, two or three groups independently selected from lower alkyl, lower alkoxy, oxo, halogen and halogenalkyl, or being condensed with a phenyl or cyclohexyl ring, said phenyl or cyclohexyl ring being unsubstituted or substituted by one, two or three groups independently selected from lower alkyl, lower alkoxy, halogen and halogenalkyl;

and pharmaceutically acceptable salts thereof.

In another embodiment of the present invention, provided is a process for the manufacture of a compound according to formula I, comprising the steps of:

reacting a compound of the formula II

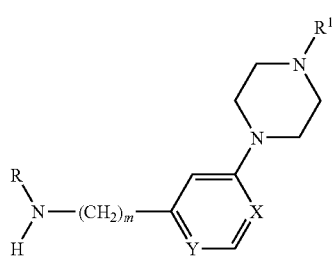

wherein X, Y, R, R¹ and m are as defined above, with a sulfonylchloride or sulfamoylchloride of the formula III

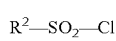

R²—SO₂—Cl      III wherein R² is as defined herein before, to obtain a compound of the formula I-A

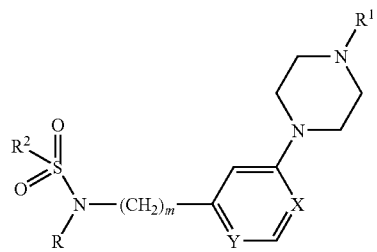

I-A wherein X, Y, R, R¹, R² and m are as defined above, or reacting a compound of the formula II

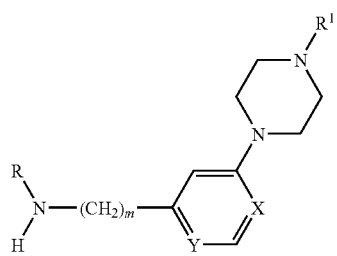

II wherein X, Y, R, R¹ and m are as defined above, with a chloride of the formula IV

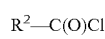

R²—C(O)Cl      IV wherein R² is as defined above, to obtain a compound of the formula I-B

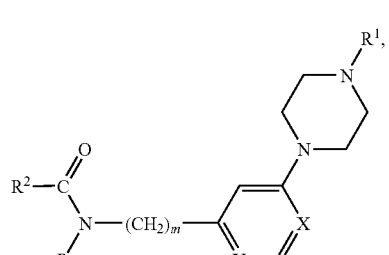

I-B wherein X, Y, R, R¹, R² and m are as defined above, or reacting a compound of the formula II

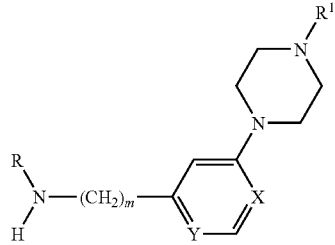

II wherein X, Y, R, R¹ and m are as defined above, with an isocyanate of the formula V

wherein R⁴ is as defined above, to obtain a compound of the formula I-C

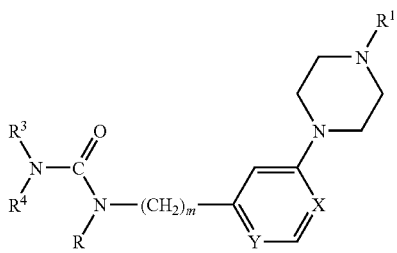

wherein R³ is hydrogen and X, Y, R, R¹, R⁴ and m are as defined above, or activating a compound of the formula II

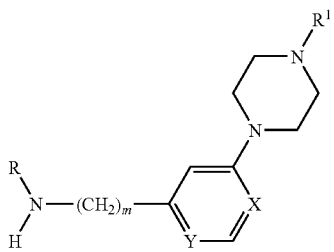

wherein X, Y, R, R¹ and m are as defined above, with phenylchloroformate to obtain a phenylcarbamate of formula

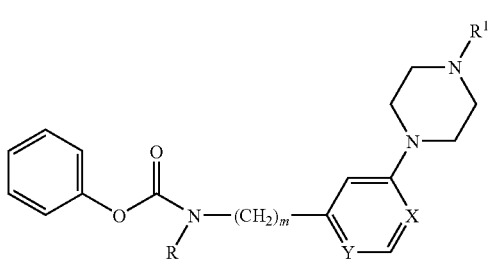

which is then reacted with an amine of formula

   VII, wherein R³ and R⁴ are as defined above, to obtain a compound of the formula I-C

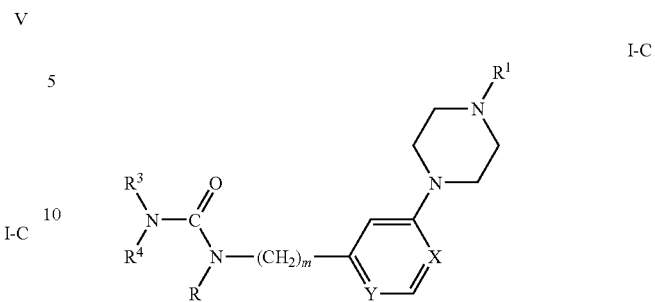

wherein X, Y, R, R¹, R³, R⁴ and m are as defined above, and if desired, converting the compound of formula I-A, I-B or I-C into a pharmaceutically acceptable salt.

In a further embodiment of the present invention, provided is a pharmaceutical composition, comprising a therapeutically effective amount of a compound according to formula I and a pharmaceutically acceptable carrier and/or adjuvant.

In a yet another embodiment of the present invention, provided is a method for the treatment and/or prevention of diseases which are associated with the modulation of H3 receptors, comprising the step of administering a therapeutically effective amount of a compound according to formula I to a human being or animal in need thereof.

DETAILED DESCRIPTION

The present invention provides, for example, selective, directly acting H3 receptor antagonists respectively inverse agonists. Such antagonists/inverse agonists are useful as therapeutically active substances, particularly in the treatment and/or prevention of diseases which are associated with the modulation of H3 receptors.

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_1$-$C_7$-alkyl", alone or in combination, signifies a straight-chain or branched-chain alkyl group with 1 to 7 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$-$C_7$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl, ethyl and isopropyl, and most preferred methyl and ethyl.

The term "lower alkenyl" or "$C_3$-$C_7$-alkenyl", alone or in combination, signifies a straight-chain or branched alkyl group comprising an olefinic bond and up to 7, preferably up to 6, particularly preferred up to 4 carbon atoms. Examples of alkenyl groups are 1-propenyl, 2-propenyl, isopropenyl, 1-butenyl, 2-butenyl, 3-butenyl and isobutenyl. A preferred example is 2-propenyl.

The term "lower alkinyl" or "$C_3$-$C_7$-alkinyl", alone or in combination, signifies a straight-chain or branched alkyl group comprising a triple bond and up to 7, preferably up to 6, particularly preferred up to 4 carbon atoms. Examples of alkinyl groups include 2-propinyl (propargyl), 1-methyl-2-propinyl, 2-butinyl, 3-butinyl, 2-pentinyl and 1-pentin-3-yl.

The term "alkoxy" refers to the group R'—O—, wherein R' is alkyl. The term "lower alkoxy" refers to the group R'—O—, wherein R' is lower alkyl and the term "lower alkyl" has the previously given significance ("$C_1$-$C_7$-alkoxy"). Examples of lower alkoxy groups are e.g. methoxy, ethoxy, n-propoxy, isopropoxy, n-butoxy, isobutoxy, sec. butoxy and tert.butoxy, preferably methoxy and ethoxy and most preferred methoxy.

The term "lower alkoxyalkyl" or "$C_1$-$C_7$-alkoxy-$C_1$-$C_7$-alkyl" refers to lower alkyl groups as defined above wherein at least one of the hydrogen atoms of the lower alkyl group is replaced by an alkoxy group as defined above. Among the preferred lower alkoxyalkyl groups are methoxymethyl, methoxyethyl and ethoxymethyl, with methoxymethyl being especially preferred.

The term "lower alkoxyalkoxy" or "$C_1$-$C_7$-alkoxy-$C_1$-$C_7$-alkoxy" refers to lower alkoxy groups as defined above wherein at least one of the hydrogen atoms of the lower alkoxy group is replaced by an alkoxy group as defined above. Among the preferred lower alkoxyalkoxy groups are methoxyethoxy, methoxypropyloxy and ethoxyethoxy, with methoxyethoxy being especially preferred.

The term "halogen" refers to fluorine, chlorine, bromine and iodine, with fluorine, chlorine and bromine being preferred.

The term "lower halogenalkyl" or "halogen-$C_1$-$C_7$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, fluoromethyl and chloromethyl, with trifluoromethyl being especially preferred.

The term "lower hydroxyalkyl" or "hydroxy-$C_1$-$C_7$-alkyl" refers to lower alkyl groups as defined above wherein at least one of the hydrogen atoms of the lower alkyl group is replaced by a hydroxy group. Examples of lower hydroxyalkyl groups are hydroxymethyl or hydroxyethyl.

The term "cycloalkyl" or "$C_3$-$C_7$-cycloalkyl" means a cycloalkyl ring containing 3 to 7 carbon atoms, such as cyclopropyl, cyclobutyl, cyclopentyl, cyclohexyl or cycloheptyl. The cycloalkyl ring may be substituted as defined herein. Especially preferred is cyclopropyl or cyclopentyl.

The term "lower cycloalkylalkyl" or "$C_3$-$C_7$-cycloalkyl-$C_1$-$C_7$-alkyl" refers to lower alkyl groups as defined above wherein at least one of the hydrogen atoms of the lower alkyl group is replaced by a cycloalkyl group as defined above. Examples of preferred lower cycloalkylalkyl groups are cyclopropylmethyl or cyclopropylmethyl.

The term "lower phenylalkyl" or "phenyl-$C_1$-$C_7$-alkyl" refers to lower alkyl groups as defined above wherein at least one of the hydrogen atoms of the lower alkyl group is replaced by a phenyl group. The phenyl ring may be substituted as defined herein. Examples of preferred lower phenylalkyl groups are benzyl, 4-methylbenzyl, 4-fluorobenzyl, 3-methoxybenzyl and 3,4-dimethoxybenzyl.

The term "form a 4-, 5-, 6- or 7-membered saturated heterocyclic ring optionally containing a further heteroatom selected from nitrogen, oxygen or sulfur" refers to a saturated N-heterocyclic ring, which may optionally contain a further nitrogen, oxygen or sulfur atom, such as azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl, or azepanyl. The heterocyclic ring may be unsubstituted or substituted by one, two or three groups independently selected from lower alkyl, lower alkoxy, oxo, halogen and halogenalkyl. The heterocyclic ring may also be condensed with a phenyl or a cyclohexyl ring, said phenyl or cyclohexyl ring being unsubstituted or substituted by one, two or three groups independently selected from lower alkyl, lower alkoxy, halogen and halogenalkyl. Examples for such condensed heterocyclic rings are 3,4-dihydro-1H-isoquinoline, octahydroquinoline, 3,4-dihydro-2H-quinoline, 1,3-dihydroisoindole and 2,3-dihydroindole.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers.

A carbon atom bonded to four nonidentical substituents is termed a "chiral center".

In detail, the present invention relates to compounds of the general formula

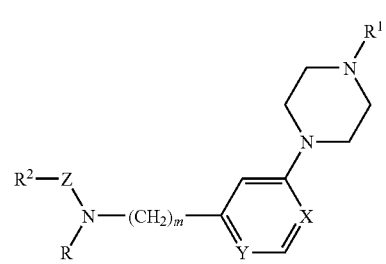

I wherein

R is hydrogen or lower alkyl;

$R^1$ is selected from the group consisting of hydrogen, lower alkyl, $C_3$-$C_7$-alkenyl, $C_3$-$C_7$-alkinyl, lower halogenalkyl, lower hydroxyalkyl, lower alkoxyalkyl, $C_3$-$C_7$-cycloalkyl and lower $C_3$-$C_7$-cycloalkylalkyl;

X is N and Y is C, or

Y is N and X is C;

m is 0 or 1;

Z is C(O) or $SO_2$;

$R^2$ is selected from the group consisting of lower alkyl, $C_3$-$C_7$-alkenyl, $C_3$-$C_7$-alkinyl, lower halogenalkyl, lower hydroxyalkyl, lower alkoxyalkyl, $C_3$-$C_7$-cycloalkyl or $C_3$-$C_7$-cycloalkyl substituted by phenyl or lower alkyl, lower $C_3$-$C_7$-cycloalkylalkyl, unsubstituted phenyl or phenyl mono- or disubstituted by lower alkyl, lower alkoxy, halogen or lower halogenalkyl, lower phenylalkyl wherein the phenyl ring is unsubstituted or mono- or disubstituted by lower alkyl, lower alkoxy, halogen or lower halogenalkyl, unsubstituted pyridyl or pyridyl mono- or disubstituted by lower alkyl, lower alkoxy, halogen or lower halogenalkyl, and

—$NR^3R^4$, or, in case Z is C(O), $R^2$ can also be lower alkoxy or lower alkoxyalkoxy;

$R^3$ is hydrogen or lower alkyl;

$R^4$ is selected from the group consisting of lower alkyl, $C_3$-$C_7$-alkenyl, $C_3$-$C_7$-alkinyl, lower alkoxyalkyl, $C_3$-$C_7$-cycloalkyl, $C_3$-$C_7$-cycloalkyl substituted by phenyl, lower $C_3$-$C_7$-cycloalkylalkyl, unsubstituted phenyl or phenyl mono- or disubstituted by lower alkyl, lower alkoxy, halogen or lower halogenalkyl, or lower phenylalkyl wherein phenyl is unsubstituted or mono- or disubstituted by lower alkyl, lower alkoxy, halogen or lower halogenalkyl; or $R^3$ and $R^4$ together with the nitrogen atom to which they are attached form a 4-, 5-, 6- or 7-membered heterocyclic ring optionally containing a further heteroatom selected from nitrogen, oxygen or sulfur, said heterocyclic ring being unsubstituted or substituted by one, two or three groups independently selected from lower alkyl, lower alkoxy, oxo, halogen and halogenalkyl, or being condensed with a phenyl or cyclohexyl ring, said phenyl or cyclohexyl ring being unsubstituted or substituted by one, two or three groups independently selected from lower alkyl, lower alkoxy, halogen and halogenalkyl;

and pharmaceutically acceptable salts thereof.

Thus, the substituent $R^1$ is selected from the group consisting of hydrogen, lower alkyl, $C_3$-$C_7$-alkenyl, $C_3$-$C_7$-alkinyl, lower halogenalkyl, lower hydroxyalkyl, lower alkoxyalkyl, $C_3$-$C_7$-cycloalkyl and lower $C_3$-$C_7$-cycloalkylalkyl. Preferred compounds of formula I according to the present invention are those, wherein $R^1$ is lower alkyl or $C_3$-$C_7$-cycloalkyl, with those compounds, wherein $R^1$ is $C_3$-$C_7$-cycloalkyl being more preferred, and those compounds, wherein $R^1$ is cyclopentyl, being most preferred. Compounds of formula I, wherein $R^1$ is ethyl or isopropyl, are also very preferred.

m is an integer of 0 or 1. Especially preferred are those compounds of formula I, wherein m is 0.

However, compounds of formula I, wherein m is 1, are also a preferred embodiment of the invention.

Preferred compounds of formula I of the present invention are those, wherein R is hydrogen and $R^2$ is selected from the group consisting of lower alkyl, $C_3$-$C_7$-alkenyl, $C_3$-$C_7$-alkinyl, lower halogenalkyl, lower hydroxyalkyl, lower alkoxyalkyl, $C_3$-$C_7$-cycloalkyl or $C_3$-$C_7$-cycloalkyl substituted by phenyl, lower $C_3$-$C_7$-cycloalkylalkyl, unsubstituted phenyl or phenyl mono- or disubstituted by lower alkyl, lower alkoxy, halogen or lower halogenalkyl, lower phenylalkyl wherein the phenyl ring is unsubstituted or mono- or disubstituted by lower alkyl, lower alkoxy, halogen or lower halogenalkyl, unsubstituted pyridyl or pyridyl mono- or disubstituted by lower alkyl, lower alkoxy, halogen or lower halogenalkyl, and —$NR^3R^4$, or, in case Z is C(O), $R^2$ can also be lower alkoxy or lower alkoxyalkoxy.

One group of preferred compounds of formula I according to the present invention are those, wherein $R^2$ is selected from the group consisting of lower alkyl, $C_3$-$C_7$-alkenyl, $C_3$-$C_7$-alkinyl, lower halogenalkyl, lower hydroxyalkyl, lower alkoxyalkyl, $C_3$-$C_7$-cycloalkyl or $C_3$-$C_7$-cycloalkyl substituted by phenyl or lower alkyl, lower $C_3$-$C_7$-cycloalkylalkyl, lower phenylalkyl wherein the phenyl ring is unsubstituted or mono- or disubstituted by lower alkyl, lower alkoxy, halogen or lower halogenalkyl, unsubstituted pyridyl or pyridyl mono- or disubstituted by lower alkyl, lower alkoxy, halogen or lower halogenalkyl, and —$NR^3R^4$, or, in case Z is C(O), $R^2$ can also be lower alkoxy or lower alkoxyalkoxy.

Within this group, compounds of formula I, wherein $R^2$ is selected from the group consisting of lower alkyl, $C_3$-$C_7$-cycloalkyl and lower alkoxyalkyl, are more preferred.

Furthermore, compounds of formula I are preferred, wherein $R^2$ is lower phenylalkyl wherein phenyl is unsubstituted or mono- or disubstituted by lower alkyl, lower alkoxy, halogen or lower halogenalkyl.

Also preferred are compounds of formula I of the present invention, wherein $R^2$ is the group —$NR^3R^4$ and $R^3$ and $R^4$ are as defined hereinbefore, with those compounds, wherein $R^3$ and $R^4$ are lower alkyl, being especially preferred.

Another group of preferred compounds of formula I are those, wherein $R^2$ is the group —$NR^3R^4$, $R^3$ is hydrogen or lower alkyl and $R^4$ is selected from the group consisting of lower alkyl, $C_3$-$C_7$-alkenyl, $C_3$-$C_7$-alkinyl, lower alkoxyalkyl, $C_3$-$C_7$-cycloalkyl, $C_3$-$C_7$-cycloalkyl substituted by phenyl, lower $C_3$-$C_7$-cycloalkylalkyl, unsubstituted phenyl or phenyl mono- or disubstituted by lower alkyl, lower alkoxy, halogen or lower halogenalkyl, and lower phenylalkyl wherein phenyl is unsubstituted or mono- or disubstituted by lower alkyl, lower alkoxy, halogen or lower halogenalkyl.

Furthermore, compounds of formula I are preferred, wherein $R^2$ is —$NR^3R^4$ and $R^3$ and $R^4$ together with the nitrogen atom to which they are attached form a 4-, 5-, 6- or 7-membered heterocyclic ring optionally containing a further heteroatom selected from nitrogen, oxygen or sulfur, said heterocyclic ring being unsubstituted or substituted by one, two or three groups independently selected from lower alkyl, lower alkoxy, oxo, halogen and lower halogenalkyl, or being condensed with a phenyl or cyclohexyl ring, said phenyl or cyclohexyl ring being unsubstituted or substituted by one, two or three groups independently selected from lower alkyl, lower alkoxy, halogen and halogenalkyl.

Especially preferred within this group are those compounds wherein $R^3$ and $R^4$ together with the nitrogen atom to which they are attached form a 5-, 6- or 7-membered heterocyclic ring. Preferably, said heterocyclic ring is unsubstituted or substituted by one or two groups independently selected from lower alkyl, halogen or lower halogenalkyl or it is condensed with a phenyl of cyclohexyl ring. Most preferably, $R^3$ and $R^4$ together with the nitrogen atom form the groups piperidine, morpholine, pyrrolidine, 2-methyl-pyrrolidine, 2-trifluormethylpyrrolidine, 2-isopropylpyrrolidine, 2-methylpiperidine, 3-methyl-piperidine, 4-methylpiperidine, 2,6-dimethylpiperidine, 4-fluoropiperidine, 4,4-difluoropiperidine, 3,3-difluoropiperidine, 4-trifluoromethylpiperidine, octahydroquinoline, 3,4-dihydro-2H-quinoline, 3,4-dihydro-1H-isoquinoline, 1,3-dihydroisoindole, 2,3-dihydroindole, and azepane.

Further preferred compounds of the present invention are those, wherein $R^2$ is the group $-NR^3R^4$, $R^3$ is hydrogen and $R^4$ is lower phenylalkyl wherein phenyl is unsubstituted or mono- or disubstituted by lower alkyl, lower alkoxy, halogen or lower halogenalkyl.

Furthermore, compounds of formula I of the present invention are preferred, wherein $R^2$ is unsubstituted phenyl or phenyl mono- or disubstituted by lower alkyl, lower alkoxy, halogen or lower halogenalkyl.

A preferred group of compounds of formula I are those, wherein Z is $SO_2$. These are the compounds having the formula

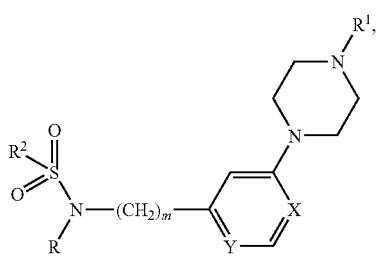

I-A wherein X, Y, R, $R^1$, $R^2$ and m are as defined hereinbefore.

Furthermore, compounds of formula I are preferred, wherein Z is C(O). These are compounds having the formula

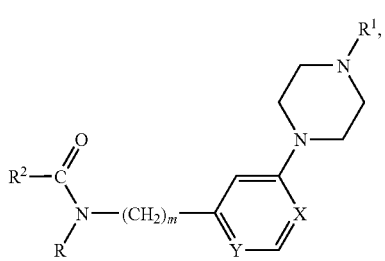

I-B wherein X, Y, R, $R^1$, $R^2$ and m are as defined hereinbefore.

Within this group, those compounds are especially preferred wherein Z is C(O) and $R^2$ is $-NR^3R^4$, thus meaning compounds of the formula

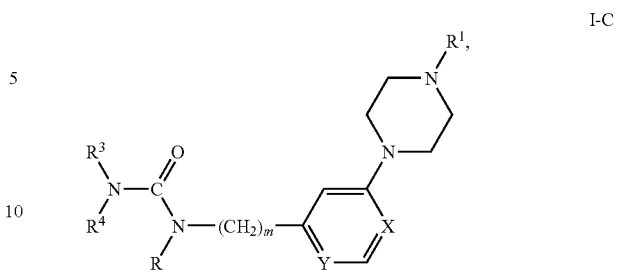

I-C wherein X, Y, R, $R^1$, $R^3$, $R^4$ and m are as defined herein before.

Compounds of formula I of the present invention are those, wherein X is N and Y is C, thus meaning compounds of the formula

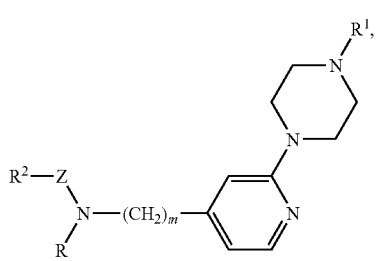

I-D wherein R, $R^1$, $R^2$, Z and m are as defined herein before.

The invention further includes compounds of formula I, wherein X is C and Y is N, thus meaning compounds of the formula

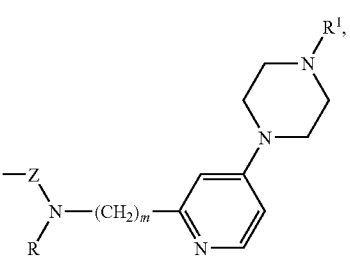

I-E wherein R, $R^1$, $R^2$, Z and m are as defined herein before.

Especially preferred are compounds of formula I according to the present invention, wherein R is hydrogen.

Also preferred are compounds of formula I, wherein R is lower alkyl, with those compounds, wherein R is methyl, being specifically preferred.

Examples of preferred compounds of formula I are the following:

1-[2-(4-ethyl-piperazin-1-yl)-pyridin-4-yl]-3-propyl-urea,
3-[2-(4-cyclopentyl-piperazin-1-yl)-pyridin-4-yl]-1,1-diethyl-urea,
N-[2-(4-ethyl-piperazin-1-yl)-pyridin-4-yl]-propionamide,
N-[2-(4-ethyl-piperazin-1-yl)-pyridin-4-yl]-butyramide,
N-[2-(4-ethyl-piperazin-1-yl)-pyridin-4-yl]-C-phenyl-methanesulfonamide,
C-(4-chloro-phenyl)-N-[2-(4-ethyl-piperazin-1-yl)-pyridin-4-yl]-methanesulfonamide, N-[2-(4-ethyl-piperazin-1-yl)-pyridin-4-yl]-3-fluoro-benzenesulfonamide,
4-chloro-N-[2-(4-ethyl-piperazin-1-yl)-pyridin-4-yl]-benzenesulfonamide,
1-[2-(4-cyclopentyl-piperazin-1-yl)-pyridin-4-yl]-3-(4-fluoro-benzyl)-urea,
N-[2-(4-cyclopentyl-piperazin-1-yl)-pyridin-4-yl]-propionamide,
N-[2-(4-cyclopentyl-piperazin-1-yl)-pyridin-4-yl]-butyramide,
cyclohexanecarboxylic acid [2-(4-cyclopentyl-piperazin-1-yl)-pyridin-4-yl]-amide,
N-[2-(4-cyclopentyl-piperazin-1-yl)-pyridin-4-yl]-3-methoxy-benzamide,
C-(4-chloro-phenyl)-N-[2-(4-cyclopentyl-piperazin-1-yl)-pyridin-4-yl]-methanesulfonamide,
cyclopropanecarboxylic acid [2-(4-cyclopentyl-piperazin-1-yl)-pyridin-4-yl]-amide,
cyclobutanecarboxylic acid [2-(4-cyclopentyl-piperazin-1-yl)-pyridin-4-yl]-amide,
cyclopentanecarboxylic acid [2-(4-cyclopentyl-piperazin-1-yl)-pyridin-4-yl]-amide,
N-[2-(4-cyclopentyl-piperazin-1-yl)-pyridin-4-yl]-2-ethyl-butyramide,
N-[2-(4-cyclopentyl-piperazin-1-yl)-pyridin-4-yl]-2-fluoro-benzamide,
N-[2-(4-cyclopentyl-piperazin-1-yl)-pyridin-4-yl]-4-fluoro-benzamide,
N-[2-(4-cyclopentyl-piperazin-1-yl)-pyridin-4-yl]-2-methoxy-benzamide,
2-chloro-N-[2-(4-cyclopentyl-piperazin-1-yl)-pyridin-4-yl]-nicotinamide,
N-[2-(4-cyclopentyl-piperazin-1-yl)-pyridin-4-yl]-2-phenyl-acetamide,
N-[2-(4-cyclopentyl-piperazin-1-yl)-pyridin-4-yl]-2-(4-fluoro-phenyl)-acetamide,
N-[2-(4-cyclopentyl-piperazin-1-yl)-pyridin-4-yl]-2-(3-methoxy-phenyl)-acetamide,
[2-(4-cyclopentyl-piperazin-1-yl)-pyridin-4-yl]-carbamic acid isobutyl ester,
1-[2-(4-cyclopentyl-piperazin-1-yl)-pyridin-4-yl]-3-propyl-urea,
cyclohexyl-3-[2-(4-cyclopentyl-piperazin-1-yl)-pyridin-4-yl]-urea,
piperidine-1-carboxylic acid [2-(4-cyclopentyl-piperazin-1-yl)-pyridin-4-yl]-amide,
morpholine-4-carboxylic acid [2-(4-cyclopentyl-piperazin-1-yl)-pyridin-4-yl]-amide,
pyrrolidine-1-carboxylic acid [2-(4-cyclopentyl-piperazin-1-yl)-pyridin-4-yl]-amide,
4,4-difluoro-piperidine-1-carboxylic acid [2-(4-cyclopentyl-piperazin-1-yl)-pyridin-4-yl]-amide,
methyl-piperidine-1-carboxylic acid [2-(4-cyclopentyl-piperazin-1-yl)-pyridin-4-yl]-amide,
methyl-piperidine-1-carboxylic acid [2-(4-cyclopentyl-piperazin-1-yl)-pyridin-4-yl]-amide,
methyl-piperidine-1-carboxylic acid [2-(4-cyclopentyl-piperazin-1-yl)-pyridin-4-yl]-amide,
2,6-dimethyl-piperidine-1-carboxylic acid [2-(4-cyclopentyl-piperazin-1-yl)-pyridin-4-yl]-amide,
fluoro-piperidine-1-carboxylic acid [2-(4-cyclopentyl-piperazin-1-yl)-pyridin-4-yl]-amide,
3,3-difluoro-piperidine-1-carboxylic acid [2-(4-cyclopentyl-piperazin-1-yl)-pyridin-4-yl]-amide,
4-trifluoromethyl-piperidine-1-carboxylic acid [2-(4-cyclopentyl-piperazin-1-yl)-pyridin-4-yl]-amide,
octahydro-quinoline-1-carboxylic acid [2-(4-cyclopentyl-piperazin-1-yl)-pyridin-4-yl]-amide,
octahydro-isoquinoline-2-carboxylic acid [2-(4-cyclopentyl-piperazin-1-yl)-pyridin-4-yl]-amide,
3,4-dihydro-2H-quinoline-1-carboxylic acid [2-(4-cyclopentyl-piperazin-1-yl)-pyridin-4-yl]-amide,
3,4-dihydro-1H-isoquinoline-2-carboxylic acid [2-(4-cyclopentyl-piperazin-1-yl)-pyridin-4-yl]-amide,
2-methyl-pyrrolidine-1-carboxylic acid [2-(4-cyclopentyl-piperazin-1-yl)-pyridin-4-yl]-amide,
2-trifluoromethyl-pyrrolidine-1-carboxylic acid [2-(4-cyclopentyl-piperazin-1-yl)-pyridin-4-yl]-amide,
2-isopropyl-pyrrolidine-1-carboxylic acid [2-(4-cyclopentyl-piperazin-1-yl)-pyridin-4-yl]-amide,
1,3-dihydro-isoindole-2-carboxylic acid [2-(4-cyclopentyl-piperazin-1-yl)-pyridin-4-yl]-amide,
2,3-dihydro-indole-1-carboxylic acid [2-(4-cyclopentyl-piperazin-1-yl)-pyridin-4-yl]-amide,
3-[2-(4-cyclopentyl-piperazin-1-yl)-pyridin-4-yl]-1-isopropyl-1-(2-methoxy-ethyl)-urea, azepane-1-carboxylic acid [2-(4-cyclopentyl-piperazin-1-yl)-pyridin-4-yl]-amide,
3-[2-(4-cyclopentyl-piperazin-1-yl)-pyridin-4-yl]-1-ethyl-1-phenyl-urea,
3-[2-(4-cyclopentyl-piperazin-1-yl)-pyridin-4-yl]-1-(4-methoxy-phenyl)-1-methyl-urea,
N-[2-(4-cyclopentyl-piperazin-1-yl)-pyridin-4-ylmethyl]-butyramide,
cyclohexanecarboxylic acid [2-(4-cyclopentyl-piperazin-1-yl)-pyridin-4-ylmethyl]-amide,
N-[2-(4-cyclopentyl-piperazin-1-yl)-pyridin-4-ylmethyl]-2-phenyl-acetamide,
N-[2-(4-cyclopentyl-piperazin-1-yl)-pyridin-4-ylmethyl]-4-fluoro-benzamide,
2-(4-chloro-phenyl)-N-[2-(4-cyclopentyl-piperazin-1-yl)-pyridin-4-ylmethyl]-3-methyl-butyramide,
1-[2-(4-cyclopentyl-piperazin-1-yl)-pyridin-4-ylmethyl]-3-propyl-urea,
cyclohexyl-3-[2-(4-cyclopentyl-piperazin-1-yl)-pyridin-4-ylmethyl]-urea,
benzyl-3-[2-(4-cyclopentyl-piperazin-1-yl)-pyridin-4-ylmethyl]-urea,
propane-1-sulfonic acid [2-(4-cyclopentyl-piperazin-1-yl)-pyridin-4-ylmethyl]-amide,
dimethylamine-1-sulfonic acid [2-(4-cyclopentyl-piperazin-1-yl)-pyridin-4-ylmethyl]-amide,
C-(4-chloro-phenyl)-N-[2-(4-cyclopentyl-piperazin-1-yl)-pyridin-4-ylmethyl]-methanesulfonamide,
N-[2-(4-cyclopentyl-piperazin-1-yl)-pyridin-4-ylmethyl]-benzenesulfonamide,
N-[4-(4-cyclopentyl-piperazin-1-yl)-pyridin-2-yl]-propionamide,
cyclopropanecarboxylic acid [4-(4-cyclopentyl-piperazin-1-yl)-pyridin-2-yl]-amide,
N-[4-(4-cyclopentyl-piperazin-1-yl)-pyridin-2-yl]-butyramide,
N-[4-(4-cyclopentyl-piperazin-1-yl)-pyridin-2-yl]-2-methoxy-acetamide,
cyclopentanecarboxylic acid [4-(4-cyclopentyl-piperazin-1-yl)-pyridin-2-yl]-amide,
N-[4-(4-cyclopentyl-piperazin-1-yl)-pyridin-2-yl]-2-ethyl-butyramide,
cyclohexanecarboxylic acid [4-(4-cyclopentyl-piperazin-1-yl)-pyridin-2-yl]-amide,
N-[4-(4-cyclopentyl-piperazin-1-yl)-pyridin-2-yl]-2-fluoro-benzamide,
N-[4-(4-cyclopentyl-piperazin-1-yl)-pyridin-2-yl]-3-fluoro-benzamide, N-[4-(4-cyclopentyl-piperazin-1-yl)-pyridin-2-yl]-4-fluoro-benzamide,
N-[4-(4-cyclopentyl-piperazin-1-yl)-pyridin-2-yl]-2-methoxy-benzamide,
N-[4-(4-cyclopentyl-piperazin-1-yl)-pyridin-2-yl]-3-methoxy-benzamide,
N-[4-(4-cyclopentyl-piperazin-1-yl)-pyridin-2-yl]-4-methoxy-benzamide,
chloro-N-[4-(4-cyclopentyl-piperazin-1-yl)-pyridin-2-yl]-nicotinamide,
[4-(4-cyclopentyl-piperazin-1-yl)-pyridin-2-yl]-carbamic acid 2-methoxy-ethyl ester,
1-[4-(4-cyclopentyl-piperazin-1-yl)-pyridin-2-yl]-3-(2-methoxy-phenyl)-urea,
1-[4-(4-cyclopentyl-piperazin-1-yl)-pyridin-2-yl]-3-(1-phenyl-ethyl)-urea,
cyclohexanecarboxylic acid [2-(4-isopropyl-piperazin-1-yl)-pyridin-4-yl]-amide,
methyl-cyclohexanecarboxylic acid [2-(4-isopropyl-piperazin-1-yl)-pyridin-4-yl]-amide,
cyclopentanecarboxylic acid [2-(4-cyclopentyl-piperazin-1-yl)-pyridin-4-yl]-methyl-amide,
methyl-cyclohexanecarboxylic acid [2-(4-cyclopentyl-piperazin-1-yl)-pyridin-4-yl]-methyl-amide,
cyclohexanecarboxylic acid [2-(4-cyclopentyl-piperazin-1-yl)-pyridin-4-yl]-methyl-amide,
methyl-cyclohexanecarboxylic acid [2-(4-isopropyl-piperazin-1-yl)-pyridin-4-yl]-methyl-amide,
cyclohexanecarboxylic acid [2-(4-isopropyl-piperazin-1-yl)-pyridin-4-yl]-methyl-amide,
piperidine-1-carboxylic acid [2-(4-cyclopentyl-piperazin-1-yl)-pyridin-4-yl]-methyl-amide,
pyrrolidine-1-carboxylic acid [2-(4-cyclopentyl-piperazin-1-yl)-pyridin-4-yl]-methyl-amide,
4,4-difluoro-piperidine-1-carboxylic acid [2-(4-cyclopentyl-piperazin-1-yl)-pyridin-4-yl]-methyl-amide,
cyclohexyl-1-[2-(4-cyclopentyl-piperazin-1-yl)-pyridin-4-yl]-1-methyl-urea,
cyclopentyl-1-[2-(4-cyclopentyl-piperazin-1-yl)-pyridin-4-yl]-1-methyl-urea, and pharmaceutically acceptable salts thereof.

Particularly preferred compounds of formula I of the present invention are the following:
1-[2-(4-cyclopentyl-piperazin-1-yl)-pyridin-4-yl]-3-(4-fluoro-benzyl)-urea,
N-[2-(4-cyclopentyl-piperazin-1-yl)-pyridin-4-yl]-butyramide,
cyclohexanecarboxylic acid [2-(4-cyclopentyl-piperazin-1-yl)-pyridin-4-yl]-amide,
cyclopentanecarboxylic acid [2-(4-cyclopentyl-piperazin-1-yl)-pyridin-4-yl]-amide,
1-[2-(4-cyclopentyl-piperazin-1-yl)-pyridin-4-yl]-3-propyl-urea,
cyclohexyl-3-[2-(4-cyclopentyl-piperazin-1-yl)-pyridin-4-yl]-urea,
piperidine-1-carboxylic acid [2-(4-cyclopentyl-piperazin-1-yl)-pyridin-4-yl]-amide,
4,4-difluoro-piperidine-1-carboxylic acid [2-(4-cyclopentyl-piperazin-1-yl)-pyridin-4-yl]-amide,
methyl-piperidine-1-carboxylic acid [2-(4-cyclopentyl-piperazin-1-yl)-pyridin-4-yl]-amide,
methyl-piperidine-1-carboxylic acid [2-(4-cyclopentyl-piperazin-1-yl)-pyridin-4-yl]-amide,
2,6-dimethyl-piperidine-1-carboxylic acid [2-(4-cyclopentyl-piperazin-1-yl)-pyridin-4-yl]-amide,
fluoro-piperidine-1-carboxylic acid [2-(4-cyclopentyl-piperazin-1-yl)-pyridin-4-yl]-amide,
octahydro-quinoline-1-carboxylic acid [2-(4-cyclopentyl-piperazin-1-yl)-pyridin-4-yl]-amide,
octahydro-isoquinoline-2-carboxylic acid [2-(4-cyclopentyl-piperazin-1-yl)-pyridin-4-yl]-amide,
azepane-1-carboxylic acid [2-(4-cyclopentyl-piperazin-1-yl)-pyridin-4-yl]-amide,
cyclopropanecarboxylic acid [4-(4-cyclopentyl-piperazin-1-yl)-pyridin-2-yl]-amide,
cyclopentanecarboxylic acid [4-(4-cyclopentyl-piperazin-1-yl)-pyridin-2-yl]-amide,
cyclohexanecarboxylic acid [4-(4-cyclopentyl-piperazin-1-yl)-pyridin-2-yl]-amide,
3-methyl-cyclohexanecarboxylic acid [2-(4-cyclopentyl-piperazin-1-yl)-pyridin-4-yl]-methyl-amide,
4,4-difluoro-piperidine-1-carboxylic acid [2-(4-cyclopentyl-piperazin-1-yl)-pyridin-4-yl]-methyl-amide, and pharmaceutically acceptable salts thereof.

Furthermore, the pharmaceutically acceptable salts of the compounds of formula I and the pharmaceutically acceptable esters of the compounds of formula I individually constitute preferred embodiments of the present invention.

Compounds of formula I may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartrate, and methanesulphonate. Preferred are the hydrochloride salts. Also solvates and hydrates of compounds of formula I and their salts form part of the present invention.

Furthermore, the N-atom of the pyridine ring can be present as an N-oxide group. Such N-oxides of compounds of formula I also form part of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises
reacting a compound of the formula II

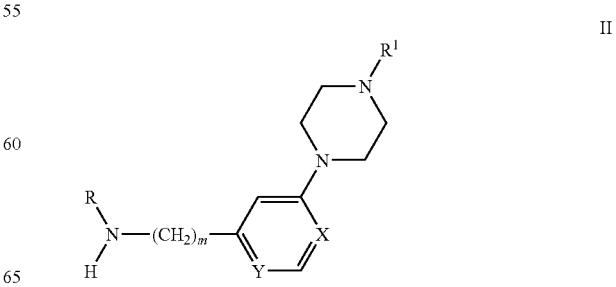

wherein X, Y, R, R¹ and m are as defined herein before, with a sulfonylchloride or sulfamoylchloride of the formula III

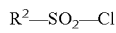   III wherein R² is as defined herein before, to obtain a compound of the formula I-B

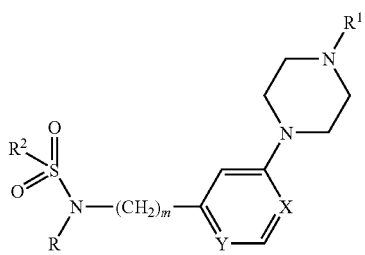

wherein X, Y, R, R¹, R² and m are as defined herein before, or reacting a compound of the formula II

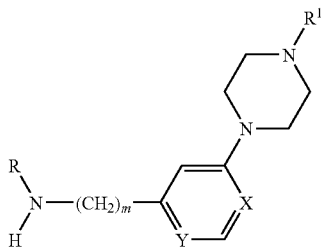   II wherein X, Y, R, R¹ and m are as defined herein before, with a chloride of the formula IV

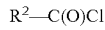   IV wherein R² is as defined herein before, to obtain a compound of the formula I-B

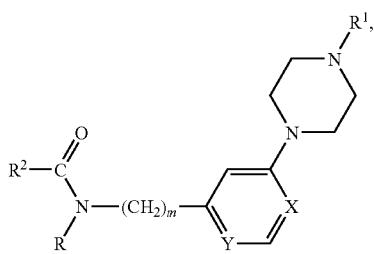   I-B wherein X, Y, R, R¹, R² and m are as defined herein before, or reacting a compound of the formula II

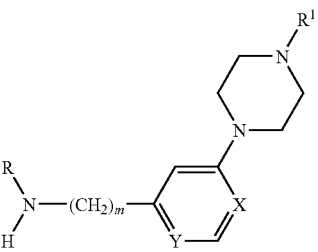   II

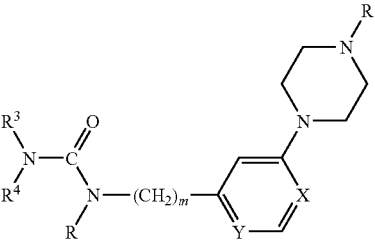   I-A wherein X, Y, R, R¹ and m are as defined herein before, with an isocyanate of the formula V $R^4-N=C=O$   V wherein R⁴ is as defined herein before, to obtain a compound of the formula I-C

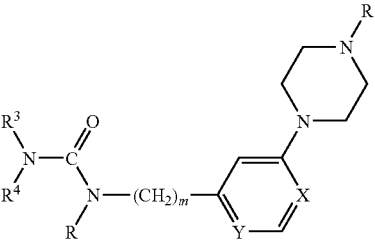   I-C wherein R³ is hydrogen and X, Y, R, R¹, R⁴ and m are as defined herein before, or activating a compound of the formula II

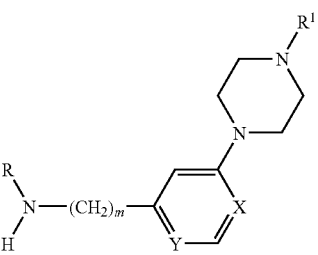   II wherein X, Y, R, R¹ and m are as defined herein before, with phenylchloroformate to obtain a phenylcarbamate of formula

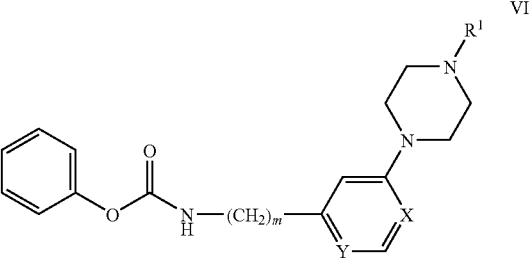   VI which is then reacted with an amine of formula

H—NR³R⁴  VII, wherein R³ and R⁴ are as defined hereinbefore, to obtain a compound of the formula I-C

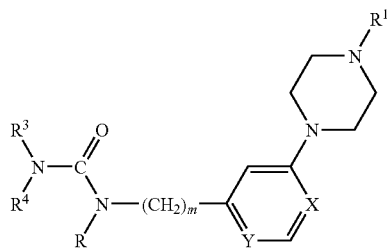

I-C wherein X, Y, R, R¹, R³, R⁴ and m are as defined herein before, and if desired, converting the compound of formula I-A, I-B or I-C into a pharmaceutically acceptable salt.

In more detail, the compounds of formula I can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

The preparation of compounds of formula I of the present invention may be carried out in sequential or convergent synthetic routes. Syntheses of the invention are shown in the following scheme. The skills required for carrying out the reaction and purification of the resulting products are known to those in the art. The substituents and indices used in the following description of the processes have the significance given herein before unless indicated to the contrary.

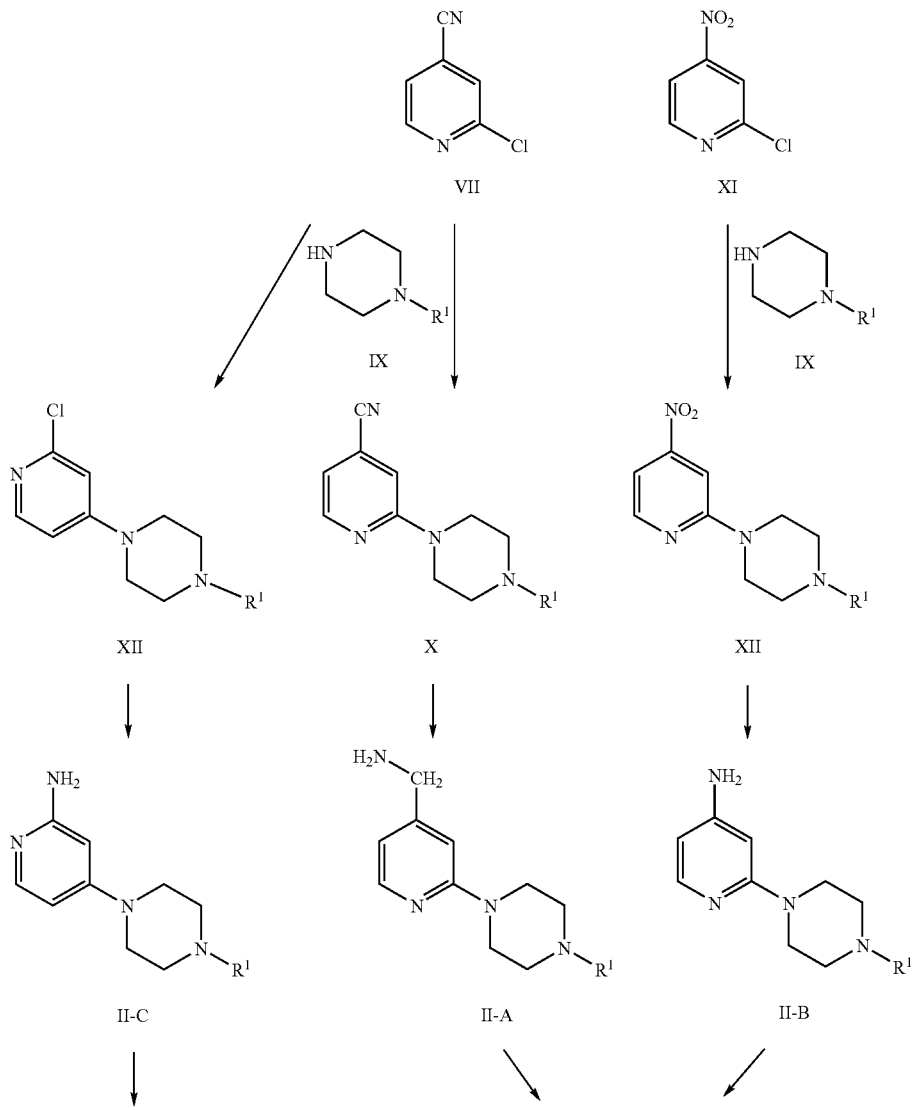

-continued

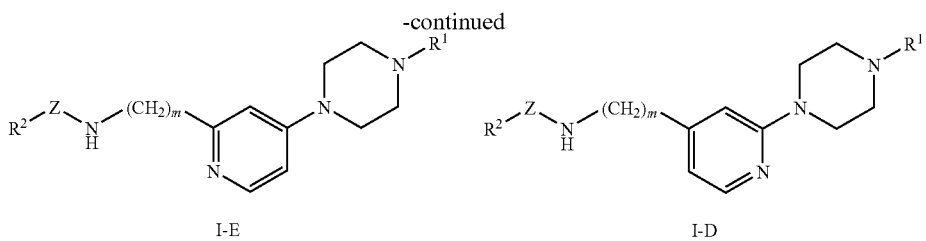

I-E          I-D

Compounds of general formula I can be prepared according to scheme 1 as follows:

The coupling of chloro substituted pyridine derivatives with piperazines is widely described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). 2-Chloro-4-cyanopyridine (VIII) or 2-chloro-4-nitropyridine (XI) can conveniently be transformed to the respective pyridine derivatives XII or X and XIII, respectively, through reaction with a piperazine derivative IX (either commercially available or accessible by methods described in references or by methods known in the art; as appropriate). The reaction can be carried out in the presence or the absence of a solvent and in the presence or the absence of a base. We find it convenient to carry out the reaction in a solvent like water and/or dimethylformamide (DMF) and in the presence of a base like diisopropyl-ethylamine (DIPEA). There is no particular restriction on the nature of the solvent to be employed, provided that it has no adverse effect on the reaction or the reagents involved and that it can dissolve the reagents, at least to some extent. Examples for suitable solvents include DMF, dichloromethane (DCM), dioxane, tetrahydrofurane (THF), and the like. There is no particular restriction on the nature of the base used in this stage, and any base commonly used in this type of reaction may equally be employed here. Examples of such bases include triethylamine and diisopropyl-ethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. A period of from 0.5 h to several days will usually suffice to yield pyridine derivatives XII or X and XIII.

The reduction of the cyano or nitro functionality in X or XII, respectively, can be achieved under various reducing reaction conditions to access the aminomethylpyridine derivatives II-A (compounds of formula II wherein m is 1) or the aminopyridine derivatives 1'-B (compounds of formula II wherein m is 0). The reaction conditions for either reaction are widely described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). We find it convenient to hydrogenate X or XII over Raney Nickel or palladium/charcoal (Pd/C) in a solvent and in the presence or absence of an acid. We find it convenient to carry out the reaction in a solvent like methanol or ethyl acetate. There is no particular restriction on the nature of the solvent to be employed, provided that it has no adverse effect on the reaction or the reagents involved and that it can dissolve the reagents, at least to some extent. Examples for suitable solvents include: methanol, ethanol, ethyl acetate, and the like. There is no particular restriction on the nature of the acid used in this stage, and any base commonly used in this type of reaction may equally be employed here. Examples of such acids include acetic acid or HCl, and the like. The reduction can be achieved through hydrogen, however any other reducing agents employed in such reaction might equally be employed here. Neither the precise hydrogen pressure nor the precise reaction temperature are critical to the invention The reaction can take place over a wide range of temperatures, and a wide range of hydrogen pressure. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield pyridine derivatives II-A (m is 1).

Starting from intermediate XIII the chloro functionality can be transformed to the respective amine by reaction with ammonia under a wide range of conditions. However, we find it convenient to react XIII with ammonia in a solvent or without a solvent in the presence or absence of copper or copper salts. There is no particular restriction on the nature of the solvent to be employed, provided that it has no adverse effect on the reaction or the reagents involved and that it can dissolve the reagents, at least to some extent. Examples for suitable solvents include methanol, ethanol, and the like. We find it convenient to carry out the reaction with heating from ambient temperature to 250° C. The time required for the reaction may also vary widely, depending on many factors, notably the reaction temperature and the nature of the reagents. However, a period of from 0.5 h to several days will usually suffice to yield aminopyridine derivatives II-C. For reaction conditions described in literature affecting such reactions see for example: Comprehensive Organic Transformations: A Guide to Functional Group Preparations, 2nd Edition, Richard C. Larock. John Wiley & Sons, New York, N.Y. 1999.

Sulfonamides, amides, carbamates and ureas can be prepared from suitable starting materials according to methods known in the art. The conversion of the amino-moiety in II-A, II-B or II-C to access sulfonamides, amides, carbamates and ureas can be affected by methods described in literature. For example the conversion of the amine derivatives II to access compounds of the general formula I is affected by reaction of II with suitable sulfonyl chlorides or sulfamoyl chlorides (compounds of formula III), or with acid chlorides, chloroformates, or carbonate esters (compounds of formula IV), or with isocyanates (compounds of formula V as defined herein before), respectively, in a solvent like dichloromethane and in the presence or the absence of a base. The compounds of formula III; IV or V are commercially available or can be prepared by known methods. There is no particular restriction on the nature of the solvent to be employed, provided that it has no adverse effect on the reaction or the reagents involved and that it can dissolve the reagents, at least to some extent. Examples for suitable solvents include chloroform, or dioxane, THF, and the like. There is no particular restriction on the nature of the base used in this stage, and any base commonly used in this type of reaction may equally be employed here. Examples of such bases include triethylamine and diisopropyl-ethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield pyridine derivatives of formula I. For reaction conditions described in literature affecting such reactions see for example: Comprehensive Organic Transformations: A Guide to Functional Group Preparations, 2nd Edition, Richard C. Larock. John Wiley & Sons, New York, N.Y. 1999.

In order to obtain compounds of formula I wherein $R^2$ is —$NR^3R^4$, as defined herein before, II can be activated under various conditions known to those in the art. However we find it convenient to activate the amine functionality in II with phenylchloroformate in order to access the respective phenyl carbamate of formula V. The reaction can be carried out in the presence or the absence of a solvent and/or a base. There is no particular restriction on the nature of the solvent to be employed, provided that it has no adverse effect on the reaction or the reagents involved and that it can dissolve the reagents, at least to some extent. Examples for suitable solvents include dichlormethane (DCM), chloroform, THF, and the like. There is no particular restriction on the nature of the base used in this stage, and any base commonly used in this type of reaction may equally be employed here. Examples of such bases include pyridine, triethylamine and diisopropyl-ethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the intermediate phenylcarbamate. Subsequently, the reaction mixture is treated with an amine of formula VI ($HNR^3R^4$, as defined herein before). The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield compounds of formula I.

Compounds of formula II-D, wherein R is lower alkyl, can be prepared from N-(2-chloropyridin-4-yl)acetamide (commercially available) or N-(4-chloropyridin-2-yl)acetamide by alkylation methods known in the art, for example by alkylation with an alkyl iodide in the presence of a strong base such as potassium hydroxide. The resulting N-alkyl-acetamide derivatives of formula XIV are then reacted with suitable piperazines of formula XV and finally the acetyl group is cleaved under strong acidic conditions (4N hydrochloric acid) to obtain the compounds of formula IIa wherein R is lower alkyl (see Scheme 2).

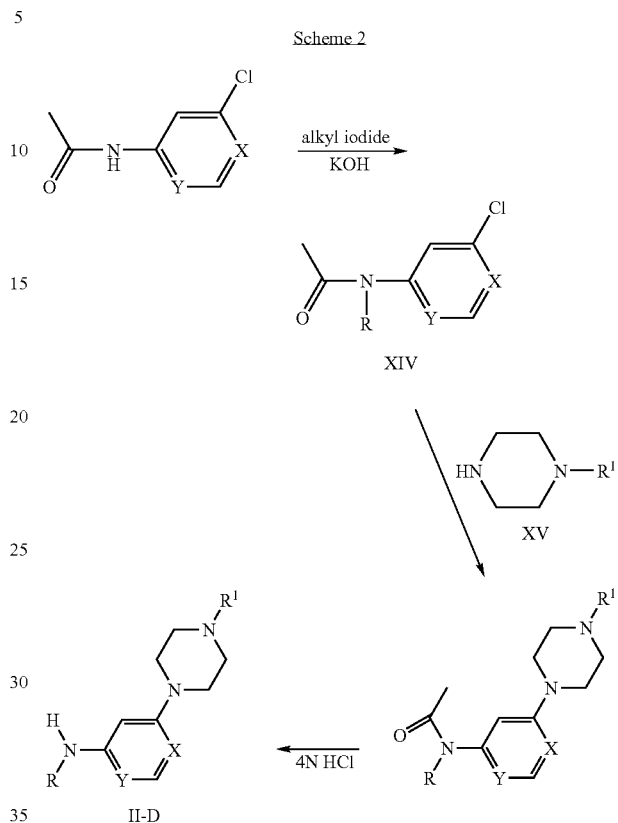

Scheme 2

As described above, the compounds of formula I of the present invention can be used as medicaments for the treatment and/or prevention of diseases which are associated with the modulation of H3 receptors, Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders. The use as medicament for the treatment and/or prevention of obesity is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of H3 receptors, Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders.

In another embodiment, the invention relates to a method for the treatment and/or prevention of diseases which are associated with the modulation of H3 receptors, Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders. A method for the treatment and/or prevention of obesity is preferred.

The invention further relates to the use of compounds of formula I as defined above for the treatment and/or prevention of diseases which are associated with the modulation of H3 receptors. Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders. The use of compounds of formula I as defined above for the treatment and/or prevention of obesity is preferred.

In addition, the invention relates to the use of compounds of formula I as defined above for the preparation of medicaments for the treatment and/or prevention of diseases which are associated with the modulation of H3 receptors Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders. The use of compounds of formula I as defined above for the preparation of medicaments for the treatment and/or prevention of obesity is preferred.

The compounds of formula I and their pharmaceutically acceptable salts possess valuable pharmacological properties. Specifically, it has been found that the compounds of the present invention are good histamine 3 receptor (H3R) antagonists and/or inverse agonists.

The following test was carried out in order to determine the activity of the compounds of formula (I).

Binding Assay with $^3$H—(R)α-Methylhistamine

Saturation binding experiments were performed using HR3-CHO membranes prepared as described in Takahashi, K, Tokita, S., Kotani, H. (2003) J. Pharmacol. Exp. Therapeutics 307, 213-218.

An appropriate amount of membrane (60 to 80 µg protein/well) was incubated with increasing concentrations of $^3$H(R) α-Methylhistamine di-hydrochloride (0.10 to 10 nM). Non specific binding was determined using a 200 fold excess of cold (R)α-Methylhistamine dihydrobromide (500 nM final concentration). The incubation was carried out at room temperature (in deep-well plates shaking for three hours). The final volume in each well was 250 µl. The incubation was followed by rapid filtration on GF/B filters (pre-soaked with 100 µl of 0.5% PEI in Tris 50 mM shaking at 200 rpm for two hours). The filtration was made using a cell-harvester and the filter plates were then washed five times with ice cold washing buffer containing 0.5 M NaCl. After harvesting, the plates were dried at 55° C. for 60 min, then we added scintillation fluid (Microscint 40, 40 microl in each well) and the amount of radioactivity on the filter was determined in Packard topcounter after shaking the plates for two hours at 200 rpm at room temperature.

Binding Buffer: 50 mM Tris-HCl pH 7.4 and 5 mM $MgCl_2 \times 6H_2O$ pH 7.4. Washing Buffer: 50 mM Tris-HCl pH 7.4 and 5 mM $MgCl_2 \times 6H_2O$ and 0.5 M NaCl pH 7.4.

Indirect measurement of affinity of H3R inverse agonists: twelve increasing concentrations (ranging from 10 µM to 0.3 nM) of the selected compounds were always tested in competition binding experiments using membrane of the human HR3-CHO cell line. An appropriate amount of protein, e.g. approximately 500 cpm binding of RAMH at Kd, were incubated for 1 hour at room temperature in 250 µl final volume in 96-well plates in presence of $^3$H(R)α-Methylhistamine (1 nM final concentration=Kd). Non-specific binding was determined using a 200 fold excess of cold (R)α-Methylhistamine dihydrobromide.

All compounds were tested at a single concentration in duplicates. Compounds that showed an inhibition of [$^3$H]-RAMH by more than 50% were tested again to determine $IC_{50}$ in a serial dilution experiment. Ki's were calculated from $IC_{50}$ based on Cheng-Prusoff equation (Cheng, Y, Prusoff, W H (1973) Biochem Pharmacol 22, 3099-3108).

The compounds of the present invention exhibit $K_i$ values within the range of about 1 nM to about 1000 nM, preferably of about 1 nM to about 100 nM, and more preferably of about 1 nM to about 30 nM. The following table shows measured values for some selected compounds of the present invention.

The following table shows measured values for some selected compounds of the present invention.

|  | $K_i$ (nM) |
| --- | --- |
| Example 11 | 8.5 |
| Example 48 | 76.7 |
| Example 66 | 48.6 |

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable salts, into a galenical administration form together with suitable, nontoxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I).

The following examples serve to illustrate the present invention in more detail. They are, however, not intended to limit its scope in any manner.

EXAMPLES

Intermediate 1

Ethyl-4-(4-nitro-pyridin-2-yl)-piperazine

A mixture of 2 g (13 mmol) 2-chloro-4-nitropyridine, 1.73 g (15 mmol) 1-ethyl-piperazine and 0.81 g (6 mmol) N,N-diisopropylethylamine (DIPEA) in 19 ml DMF and 20 ml water was heated to 100° C. for 24 h. The precipitate was filtered off and washed three times with 4 ml of water and dried for 24 h under vacuum to yield 2.03 g (68%) of the title compound as yellow oil (m/e): 236.7 (MH$^+$; 100%).

Intermediate 2

2-(4-Ethyl-piperazin-1-yl)-pyridin-4-ylamine

A solution of 2.03 g (9 mmol) 1-ethyl-4-(4-nitro-pyridin-2-yl)-piperazine in 30 ml methanol was hydrogenated over 0.052 g Pd/C with 1 bar hydrogen for 3 h at room temperature. The mixture was filtered and evaporated to dryness to yield the title compound as yellow solid which was used without further purification (m/e): 207.1 (MH$^+$; 100%).

Intermediate 3

Cyclopentyl-4-(4-nitro-pyridin-2-yl)-piperazine and Intermediate 4

1-(2-Chloro-pyridin-4-yl)-4-cyclopentyl-piperazine

A mixture of 5.6 g (35 mmol) 2-chloro-4-nitropyridine, 5.75 g (37 mmol) 1-cyclo-pentyl piperazine and 4.59 g (35 mmol) N,N-diisopropylethylamine in 35 ml DMF and 12 ml water was heated to 95° C. for 3 h. After evaporation to dryness the residue was taken up in 150 ml NaHCO$_3$ aq. and 150 ml ethyl acetate. The aqueous phase was extracted two times with 150 ml ethyl acetate each and the combined organic phases were washed twice with 100 ml NaHCO$_3$ aq each and 100 ml NaCl aq. sat. and dried with MgSO$_4$ and evaporated to dryness. The residue was purified with column chromatography to yield 2.85 g (29%) 1-cyclopentyl-4-(4-nitro-pyridin-2-yl)-piperazine (m/e): 277.3 (MH$^+$; 100%) and 4.47 g (47%) 1-(2-chloro-pyridin-4-yl)-4-cyclopentyl-piperazine (m/e): 266.3 (MH$^+$; 100%).

Intermediate 5

2-(4-Cyclopentyl-piperazin-1-yl)-pyridin-4-ylamine

A mixture of 2.85 g (10 mmol) 1-cyclopentyl-4-(4-nitro-pyridin-2-yl)-piperazine and 0.285 g Pd/C (10%) in 25 ml methanol was treated with 1 bar hydrogen at room temperature for 3 h. After filtration the mixture was evaporated to dryness to yield 2.34 g (92%) of the title compound as brownish solid. (m/e): 247.4 (MH$^+$; 100%).

Intermediate 6

4-(4-Cyclopentyl-piperazin-1-yl)-pyridin-2-ylamine

A mixture of 5.84 g (22 mmol) 1-(2-chloro-pyridin-4-yl)-4-cyclopentyl-piperazine, 0.8 g copper powder in 41 ml 7M ammonia in methanol was heated to 150° C. for 18 h. After evaporation to dryness the residue was purified on silica eluting with a gradient formed from dichloromethane/methanol and NEt$_3$. The evaporation of the combined product fractions yielded 1.29 g (24%) of the title compound as yellowish solid. (m/e): 247.3 (MH$^+$; 100%).

Intermediate 7

2-(4-Cyclopentyl-piperazin-1-yl)-isonicotinonitrile

A mixture of 2 g (14 mmol) 2-chloro-4-cyanopyridine and 2.34 g (15 mmol) 1-cyclopentylpiperazine in 5 ml DMF was heated to 80° C. for 16 h. The mixture was evaporated under reduced pressure and the residue was treated with 100 ml 1M NaHCO$_3$ aq. and extracted with two times 100 ml ethyl acetate. The combined organic phases were dried with MgSO$_4$ and evaporated under reduced pressure to yield 3.4 g (92%) of the title compound as grey solid. (m/e): 257.3 (MH$^+$; 100%).

Intermediate 8

C-[2-(4-Cyclopentyl-piperazin-1-yl)-pyridin-4-yl]-methylamine

A solution of 2.8 g (11 mmol) 2-(4-cyclopentyl-piperazin-1-yl)-isonicotinonitrile in 10 ml methanol, 15 ml ethyl acetate and 5 ml ammonia was hydrogenated over Raney Nickel with 1 bar hydrogen at 30° C. for 4 h. The mixture was filtered and the residue was washed with 20 ml ethyl acetate three times. After evaporation of the organic phase the residue was purified with preparative HPLC on reversed phase to yield after evaporation of the combined product fractions 1.21 g (42%) of the title compound as yellow solid. (m/e): 261.3 (MH$^+$; 100%).

Example 1

1-[2-(4-Ethyl-piperazin-1-yl)-pyridin-4-yl]-3-propyl-urea

A mixture of 20.6 mg (0.1 mmol) 2-(4-ethyl-piperazin-1-yl)-pyridin-4-ylamine, 15 mg (0.15 mmol) triethylamine and 9.4 mg (0.11 mmol) 1-isocyanato-propane in 1 ml dichloromethane was stirred at room temperature for 16 h. After evaporation the residue was taken up in 1 ml methanol/acetonitrile 1/1 and subjected to preparative HPLC purification on reversed phase eluting with a gradient of acetonitrile/water (0.05% triethylamine). The combined product fractions were evaporated to dryness to yield 7.2 mg (25%) of the title compound. (m/e): 292.3 (MH$^+$; 100%).

According to the procedure described for the synthesis of Example 1 further pyridine derivatives have been synthesized from the intermediates 2, 5, 6 and 8, respectively, and commercially available reagents listed in table 1. The examples are compiled in table 1 and comprise Example No. 2 to Example No. 56.

TABLE 1

| No | MW | Name | Starting materials | MH$^+$ found |
|---|---|---|---|---|
| 2 | 262.36 | N-[2-(4-ethyl-piperazin-1-yl)-pyridin-4-yl]-propionamide | 2-(4-ethyl-piperazin-1-yl)-pyridin-4-ylamine (intermediate 2) and propionyl chloride | 263.1 |
| 3 | 276.38 | N-[2-(4-ethyl-piperazin-1-yl)-pyridin-4-yl]-butyramide | 2-(4-ethyl-piperazin-1-yl)-pyridin-4-ylamine (intermediate 2) and butyryl chloride | 277.3 |
| 4 | 360.48 | N-[2-(4-ethyl-piperazin-1-yl)-pyridin-4-yl]-C-phenyl-methanesulfonamide | 2-(4-ethyl-piperazin-1-yl)-pyridin-4-ylamine (intermediate 2) and phenyl-methanesulfonyl chloride | 361.3 |
| 5 | 394.92 | C-(4-chloro-phenyl)-N-[2-(4-ethyl-piperazin-1-yl)-pyridin-4-yl]-methanesulfonamide | 2-(4-ethyl-piperazin-1-yl)-pyridin-4-ylamine (intermediate 2) and (4-chloro-phenyl)-methanesulfonyl chloride | 395.2 |
| 6 | 364.44 | N-[2-(4-ethyl-piperazin-1-yl)-pyridin-4-yl]-3-fluoro-benzenesulfonamide | 2-(4-ethyl-piperazin-1-yl)-pyridin-4-ylamine (intermediate 2) and 3-fluoro-benzenesulfonyl chloride | 365.1 |
| 7 | 380.9 | 4-chloro-N-[2-(4-ethyl-piperazin-1-yl)-pyridin-4-yl]-benzenesulfonamide | 2-(4-ethyl-piperazin-1-yl)-pyridin-4-ylamine (intermediate 2) and 4-chloro-benzenesulfonyl chloride | 381.3 |
| 8 | 397.5 | 1-[2-(4-cyclopentyl-piperazin-1-yl)-pyridin-4-yl]-3-(4-fluoro-benzyl)-urea | 2-(4-cyclopentyl-piperazin-1-yl)-pyridin-4-ylamine (intermediate 5) and 1-fluoro-4-isocyanatomethyl-benzene | 398.4 |
| 9 | 302.42 | N-[2-(4-cyclopentyl-piperazin-1-yl)-pyridin-4-yl]-propionamide | 2-(4-cyclopentyl-piperazin-1-yl)-pyridin-4-ylamine (intermediate 5) and propionyl chloride | 303.2 |
| 10 | 316.45 | N-[2-(4-cyclopentyl-piperazin-1-yl)-pyridin-4-yl]-butyramide | 2-(4-cyclopentyl-piperazin-1-yl)-pyridin-4-ylamine (intermediate 5) and butyryl chloride | 317.2 |
| 11 | 356.51 | cyclohexanecarboxylic acid [2-(4-cyclopentyl-piperazin-1-yl)-pyridin-4-yl]-amide | 2-(4-cyclopentyl-piperazin-1-yl)-pyridin-4-ylamine (intermediate 5) and cyclohexanecarbonyl chloride | 357.3 |
| 12 | 380.49 | N-[2-(4-cyclopentyl-piperazin-1-yl)-pyridin-4-yl]-3-methoxy-benzamide | 2-(4-cyclopentyl-piperazin-1-yl)-pyridin-4-ylamine (intermediate 5) and 3-methoxy-benzoyl chloride | 381.3 |
| 13 | 434.99 | C-(4-chloro-phenyl)-N-[2-(4-cyclopentyl-piperazin-1-yl)-pyridin-4-yl]-methanesulfonamide | 2-(4-cyclopentyl-piperazin-1-yl)-pyridin-4-ylamine (intemediate 5) and (4-Chloro-phenyl)-methanesulfonyl chloride | 435.4 |
| 14 | 314.43 | cyclopropanecarboxylic acid [2-(4-cyclopentyl-piperazin-1-yl)-pyridin-4-yl]-amide | 2-(4-cyclopentyl-piperazin-1-yl)-pyridin-4-ylamine (intermediate 5) and cyclopropanecarbonyl chloride | 315.2 |
| 15 | 328.46 | cyclobutanecarboxylic acid [2-(4-cyclopentyl- | 2-(4-cyclopentyl-piperazin-1-yl)-pyridin-4-ylamine (intemediate 5) | 329.4 |

TABLE 1-continued

| No | MW | Name | Starting materials | MH+ found |
|---|---|---|---|---|
| | | piperazin-1-yl)-pyridin-4-yl]-amide | and cyclobutanecarbonyl chloride | |
| 16 | 342.49 | cyclopentanecarboxylic acid [2-(4-cyclopentyl-piperazin-1-yl)-pyridin-4-yl]-amide | 2-(4-cyclopentyl-piperazin-1-yl)-pyridin-4-ylamine (intemediate 5) and cyclopentanecarbonyl chloride | 343.3 |
| 17 | 344.5 | N-[2-(4-cyclopentyl-piperazin-1-yl)-pyridin-4-yl]-2-ethyl-butyramide | 2-(4-cyclopentyl-piperazin-1-yl)-pyridin-4-ylamine (intemediate 5) and 2-ethyl-butyryl chloride | 345.3 |
| 18 | 368.46 | N-[2-(4-cyclopentyl-piperazin-1-yl)-pyridin-4-yl]-2-fluoro-benzamide | 2-(4-cyclopentyl-piperazin-1-yl)-pyridin-4-ylamine (intemediate 5) and 2-fluoro-benzoyl chloride | 369.2 |
| 19 | 368.46 | N-[2-(4-cyclopentyl-piperazin-1-yl)-pyridin-4-yl]-4-fluoro-benzamide | 2-(4-cyclopentyl-piperazin-1-yl)-pyridin-4-ylamine (intemediate 5) and 4-fluoro-benzoyl chloride | 369.2 |
| 20 | 380.49 | N-[2-(4-cyclopentyl-piperazin-1-yl)-pyridin-4-yl]-2-methoxy-benzamide | 2-(4-cyclopentyl-piperazin-1-yl)-pyridin-4-ylamine (intemediate 5) and 2-methoxy-benzoyl chloride | 381.4 |
| 21 | 385.9 | 2-chloro-N-[2-(4-cyclopentyl-piperazin-1-yl)-pyridin-4-yl]-nicotinamide | 2-(4-cyclopentyl-piperazin-1-yl)-pyridin-4-ylamine (intemediate 5) and 2-chloro-nicotinoyl chloride | 386.3 |
| 22 | 364.49 | N-[2-(4-cyclopentyl-piperazin-1-yl)-pyridin-4-yl]-2-phenyl-acetamide | 2-(4-cyclopentyl-piperazin-1-yl)-pyridin-4-ylamine (intemediate 5) and phenylacetyl chloride | 365.4 |
| 23 | 382.48 | N-[2-(4-cyclopentyl-piperazin-1-yl)-pyridin-4-yl]-2-(4-fluoro-phenyl)-acetamide | 2-(4-cyclopentyl-piperazin-1-yl)-pyridin-4-ylamine (intemediate 5) and (4-fluoro-phenyl)-acetyl chloride | 383.4 |
| 24 | 394.52 | N-[2-(4-cyclopentyl-piperazin-1-yl)-pyridin-4-yl]-2-(3-methoxy-phenyl)-acetamide | 2-(4-cyclopentyl-piperazin-1-yl)-pyridin-4-ylamine (intemediate 5) and (3-methoxy-phenyl)-acetyl chloride | 395.3 |
| 25 | 346.47 | [2-(4-cyclopentyl-piperazin-1-yl)-pyridin-4-yl]-carbamic acid isobutyl ester | 2-(4-cyclopentyl-piperazin-1-yl)-pyridin-4-ylamine (intemediate 5) and isobutylchlroformate | 347.2 |
| 26 | 331.46 | 1-[2-(4-cyclopentyl-piperazin-1-yl)-pyridin-4-yl]-3-propyl-urea | 2-(4-cyclopentyl-piperazin-1-yl)-pyridin-4-ylamine (intemediate 5) and 1-isocyanato-propane | 332.3 |
| 27 | 371.53 | 1-cyclohexyl-3-[2-(4-cyclopentyl-piperazin-1-yl)-pyridin-4-yl]-urea | 2-(4-cyclopentyl-piperazin-1-yl)-pyridin-4-ylamine (intemediate 5) and 1-isocyanato-cyclohexane | 372.3 |
| 28 | 330.48 | N-[2-(4-cyclopentyl-piperazin-1-yl)-pyridin-4-ylmethyl]-butyramide | C-[2-(4-cyclopentyl-piperazin-1-yl)-pyridin-4-yl]-methylamine (intemediate 8) and propionyl chloride | 331.5 |
| 29 | 370.54 | cyclohexanecarboxylic acid [2-(4-cyclopentyl-piperazin-1-yl)-pyridin-4-ylmethyl]-amide | C-[2-(4-cyclopentyl-piperazin-1-yl)-pyridin-4-yl]-methylamine (intemediate 8) and cyclohexanecarbonyl chloride | 357.4 |
| 30 | 378.52 | N-[2-(4-cyclopentyl-piperazin-1-yl)-pyridin-4-ylmethyl]-2-phenyl-acetamide | C-[2-(4-cyclopentyl-piperazin-1-yl)-pyridin-4-yl]-methylamine (intemediate 8) and phenylacetyl chloride | 379.3 |
| 31 | 382.48 | N-[2-(4-cyclopentyl-piperazin-1-yl)-pyridin-4-ylmethyl]-4-fluoro-benzamide | C-[2-(4-cyclopentyl-piperazin-1-yl)-pyridin-4-yl]-methylamine (intemediate 8) and 4-fluoro-benzoyl chloride | 383.3 |
| 32 | 455.05 | 2-(4-chloro-phenyl)-N-[2-(4-cyclopentyl-piperazin-1-yl)-pyridin-4-ylmethyl]-3-methyl-butyramide | C-[2-(4-cyclopentyl-piperazin-1-yl)-pyridin-4-yl]-methylamine (intemediate 8) and 2-(4-chloro-phenyl)-3-methyl-butyryl chloride | 455.6 |
| 33 | 345.49 | 1-[2-(4-cyclopentyl-piperazin-1-yl)-pyridin-4-ylmethyl]-3-propyl-urea | C-[2-(4-cyclopentyl-piperazin-1-yl)-pyridin-4-yl]-methylamine (intemediate 8) and 1-isocyanato-propane | 346.3 |

TABLE 1-continued

| No | MW | Name | Starting materials | MH+ found |
|---|---|---|---|---|
| 34 | 385.56 | 1-cyclohexyl-3-[2-(4-cyclopentyl-piperazin-1-yl)-pyridin-4-ylmethyl]-urea | C-[2-(4-cyclopentyl-piperazin-1-yl)-pyridin-4-yl]-methylamine (intemediate 8) and 1-isocyanato-cyclohexane | 386.4 |
| 35 | 393.53 | 1-benzyl-3-[2-(4-cyclopentyl-piperazin-1-yl)-pyridin-4-ylmethyl]-urea | C-[2-(4-cyclopentyl-piperazin-1-yl)-pyridin-4-yl]-methylamine (intemediate 8) and isocyanatomethyl-benzene | 394.1 |
| 36 | 366.53 | propane-1-sulfonic acid [2-(4-cyclopentyl-piperazin-1-yl)-pyridin-4-ylmethyl]-amide | C-[2-(4-cyclopentyl-piperazin-1-yl)-pyridin-4-yl]-methylamine (intemediate 8) and propane-1-sulfonyl chloride | 368.1 |
| 37 | 367.52 | dimethylamine-1-sulfonic acid [2-(4-cyclopentyl-piperazin-1-yl)-pyridin-4-ylmethyl]-amide | C-[2-(4-cyclopentyl-piperazin-1-yl)-pyridin-4-yl]-methylamine (intemediate 8) and dimethylamino-1-sulfonyl chloride | 367.3 |
| 38 | 449.02 | C-(4-chloro-phenyl)-N-[2-(4-cyclopentyl-piperazin-1-yl)-pyridin-4-ylmethyl]-methanesulfonamide | C-[2-(4-cyclopentyl-piperazin-1-yl)-pyridin-4-yl]-methylamine (intemediate 8) and (4-chloro-phenyl)-methanesulfonyl chloride | 449 |
| 39 | 400.54 | N-[2-(4-cyclopentyl-piperazin-1-yl)-pyridin-4-ylmethyl]-benzenesulfonamide | C-[2-(4-cyclopentyl-piperazin-1-yl)-pyridin-4-yl]-methylamine (intemediate 8) and benzenesulfonyl chloride | 401.1 |
| 40 | 302.42 | N-[4-(4-cyclopentyl-piperazin-1-yl)-pyridin-2-yl]-propionamide | 4-(4-cyclopentyl-piperazin-1-yl)-pyridin-2-ylamine (intemediate 6) and propionyl chloride | 303.4 |
| 41 | 314.43 | cyclopropanecarboxylic acid [4-(4-cyclopentyl-piperazin-1-yl)-pyridin-2-yl]-amide | 4-(4-cyclopentyl-piperazin-1-yl)-pyridin-2-ylamine (intemediate 6) and cyclopropanecarbonyl chloride | 315.2 |
| 42 | 316.45 | N-[4-(4-cyclopentyl-piperazin-1-yl)-pyridin-2-yl]-butyramide | 4-(4-cyclopentyl-piperazin-1-yl)-pyridin-2-ylamine (intemediate 6) and butyryl chloride | 317.3 |
| 43 | 318.42 | N-[4-(4-cyclopentyl-piperazin-1-yl)-pyridin-2-yl]-2-methoxy-acetamide | 4-(4-cyclopentyl-piperazin-1-yl)-pyridin-2-ylamine (intemediate 6) and methoxy-acetyl chloride | 319.3 |
| 44 | 342.49 | cyclopentanecarboxylic acid [4-(4-cyclopentyl-piperazin-1-yl)-pyridin-2-yl]-amide | 4-(4-cyclopentyl-piperazin-1-yl)-pyridin-2-ylamine (intemediate 6) and cyclopentanecarbonyl chloride | 343.3 |
| 45 | 344.5 | N-[4-(4-cyclopentyl-piperazin-1-yl)-pyridin-2-yl]-2-ethyl-butyramide | 4-(4-cyclopentyl-piperazin-1-yl)-pyridin-2-ylamine (intemediate 6) and 2-ethyl-butyryl chloride | 345.3 |
| 46 | 356.51 | cyclohexanecarboxylic acid [4-(4-cyclopentyl-piperazin-1-yl)-pyridin-2-yl]-amide | 4-(4-cyclopentyl-piperazin-1-yl)-pyridin-2-ylamine (intemediate 6) and cyclohexanecarbonyl chloride | 357.3 |
| 47 | 368.46 | N-[4-(4-cyclopentyl-piperazin-1-yl)-pyridin-2-yl]-2-fluoro-benzamide | 4-(4-cyclopentyl-piperazin-1-yl)-pyridin-2-ylamine (intemediate 6) and 2-fluoro-benzoyl chloride | 369.2 |
| 48 | 368.46 | N-[4-(4-cyclopentyl-piperazin-1-yl)-pyridin-2-yl]-3-fluoro-benzamide | 4-(4-cyclopentyl-piperazin-1-yl)-pyridin-2-ylamine (intemediate 6) and 3-fluoro-benzoyl chloride | 369.2 |
| 49 | 368.46 | N-[4-(4-cyclopentyl-piperazin-1-yl)-pyridin-2-yl]-4-fluoro-benzamide | 4-(4-cyclopentyl-piperazin-1-yl)-pyridin-2-ylamine (intemediate 6) and 4-fluoro-benzoyl chloride | 369.2 |
| 50 | 380.49 | N-[4-(4-cyclopentyl-piperazin-1-yl)-pyridin-2-yl]-2-methoxy-benzamide | 4-(4-cyclopentyl-piperazin-1-yl)-pyridin-2-ylamine (intemediate 6) and 2-methoxy-benzoyl chloride | 381.4 |
| 51 | 380.49 | N-[4-(4-cyclopentyl-piperazin-1-yl)-pyridin-2-yl]-3-methoxy-benzamide | 4-(4-cyclopentyl-piperazin-1-yl)-pyridin-2-ylamine (intemediate 6) and 3-methoxy-benzoyl chloride | 381.4 |

TABLE 1-continued

| No | MW | Name | Starting materials | MH+ found |
|---|---|---|---|---|
| 52 | 380.49 | N-[4-(4-cyclopentyl-piperazin-1-yl)-pyridin-2-yl]-4-methoxy-benzamide | 4-(4-cyclopentyl-piperazin-1-yl)-pyridin-2-ylamine (intemediate 6) and 4-methoxy-benzoyl chloride | 381.4 |
| 53 | 385.9 | 2-chloro-N-[4-(4-cyclopentyl-piperazin-1-yl)-pyridin-2-yl]-nicotinamide | 4-(4-cyclopentyl-piperazin-1-yl)-pyridin-2-ylamine (intemediate 6) and 2-chloro-nicotinoyl chloride | 386.3 |
| 54 | 348.45 | [4-(4-cyclopentyl-piperazin-1-yl)-pyridin-2-yl]-carbamic acid 2-methoxy-ethyl ester | 4-(4-cyclopentyl-piperazin-1-yl)-pyridin-2-ylamine (intemediate 6) and 2-methoxyethyl chloroformate | 349.4 |
| 55 | 395.51 | 1-[4-(4-cyclopentyl-piperazin-1-yl)-pyridin-2-yl]-3-(2-methoxy-phenyl)-urea | 4-(4-cyclopentyl-piperazin-1-yl)-pyridin-2-ylamine (intemediate 6) and 1-isocyanato-2-methoxy-benzene | 295.33 |
| 56 | 393.53 | 1-[4-(4-cyclopentyl-piperazin-1-yl)-pyridin-2-yl]-3-(1-phenyl-ethyl)-urea | 4-(4-cyclopentyl-piperazin-1-yl)-pyridin-2-ylamine (intemediate 6) and (1-isocyanato-ethyl)-benzene | 394.2 |

Example 57

3-[2-(4-Cyclopentyl-piperazin-1-yl)-pyridin-4-yl]-1,1-diethyl-urea

A mixture of 0.18 g (0.73 mmol) 2-(4-cyclopentyl-piperazin-1-yl)-pyridin-4-ylamine 0.12 g (0.74 mmol) phenylchloroformate and 0.11 g (1.4 mmol) pyridine in 6 ml dichloromethane and reacted at room temperature for 1.5 h and the intermediately built [2-(4-cyclopentyl-piperazin-1-yl)-pyridin-4-yl]-carbamic acid phenyl ester ((m/e): 367.4 (MH+; 100%)) was used without further purification. 1 ml of the solution was mixed with 26.7 mg (0.36 mmol) diethylamine and reacted at room temperature for 16 h. After evaporation of all volatiles the residue was taken up in acetonitrile/DMF and subjected to reversed phase preparative HPLC purification on reversed phase eluting with an acetonitrile/water/NEt$_3$ gradient to yield after evaporation of the product fractions 10.8 mg (53%) of the title compound (m/e): 346.5 (MH+; 100%).

According to the procedure described for the synthesis of Example 57 (activation with phenylchloroformate) further pyridine derivatives have been synthesized from the intermediates 2, 5, 6 and 8 respectively and commercially available reagents listed in table 2. The examples are compiled in table 2 and comprise Example No. 58 to Example No. 81.

TABLE 2

| No | MW | Name | Starting materials | MH+ found |
|---|---|---|---|---|
| 58 | 357.5 | piperidine-1-carboxylic acid [2-(4-cyclopentyl-piperazin-1-yl)-pyridin-4-yl]-amide | 2-(4-cyclopentyl-piperazin-1-yl)-pyridin-4-ylamine (intemediate 5) and piperidine | 358.1 |
| 59 | 359.47 | morpholine-4-carboxylic acid [2-(4-cyclopentyl-piperazin-1-yl)-pyridin-4-yl]-amide | 2-(4-cyclopentyl-piperazin-1-yl)-pyridin-4-ylamine (intemediate 5) and morpholine | 360.5 |
| 60 | 343.47 | pyrrolidine-1-carboxylic acid [2-(4-cyclopentyl-piperazin-1-yl)-pyridin-4-yl]-amide | 2-(4-cyclopentyl-piperazin-1-yl)-pyridin-4-ylamine (intemediate 5) and pyrrolidine | 344.1 |
| 61 | 393.48 | 4,4-difluoro-piperidine-1-carboxylic acid [2-(4-cyclopentyl-piperazin-1-yl)-pyridin-4-yl]-amide | 2-(4-cyclopentyl-piperazin-1-yl)-pyridin-4-ylamine (intemediate 5) and 4,4-difluoro-piperidine | 394.1 |
| 62 | 371.53 | 2-methyl-piperidine-1-carboxylic acid [2-(4-cyclopentyl-piperazin-1-yl)-pyridin-4-yl]-amide | 2-(4-cyclopentyl-piperazin-1-yl)-pyridin-4-ylamine (intemediate 5) and 2-methylpiperidine | 372.3 |
| 63 | 371.53 | 3-methyl-piperidine-1-carboxylic acid [2-(4-cyclopentyl-piperazin-1-yl)-pyridin-4-yl]-amide | 2-(4-cyclopentyl-piperazin-1-yl)-pyridin-4-ylamine (intemediate 5) and 3-methylpiperidine | 372.3 |
| 64 | 371.53 | 4-methyl-piperidine-1-carboxylic acid [2-(4-cyclopentyl-piperazin-1-yl)-pyridin-4-yl]-amide | 2-(4-cyclopentyl-piperazin-1-yl)-pyridin-4-ylamine (intemediate 5) and 4-methylpiperidine | 372.3 |

TABLE 2-continued

| No | MW | Name | Starting materials | MH+ found |
|---|---|---|---|---|
| 65 | 385.56 | 2,6-dimethyl-piperidine-1-carboxylic acid [2-(4-cyclopentyl-piperazin-1-yl)-pyridin-4-yl]-amide | 2-(4-cyclopentyl-piperazin-1-yl)-pyridin-4-ylamine (intemediate 5) and 2,6-dimethylpiperidine | 386.3 |
| 66 | 375.49 | 4-fluoro-piperidine-1-carboxylic acid [2-(4-cyclopentyl-piperazin-1-yl)-pyridin-4-yl]-amide | 2-(4-cyclopentyl-piperazin-1-yl)-pyridin-4-ylamine (intemediate 5) and 4-fluoro-piperidine | 376.4 |
| 67 | 393.48 | 3,3-difluoro-piperidine-1-carboxylic acid [2-(4-cyclopentyl-piperazin-1-yl)-pyridin-4-yl]-amide | 2-(4-cyclopentyl-piperazin-1-yl)-pyridin-4-ylamine (intemediate 5) and 3,3-difluoro-piperidine | 394.4 |
| 68 | 425.5 | 4-trifluoromethyl-piperidine-1-carboxylic acid [2-(4-cyclopentyl-piperazin-1-yl)-pyridin-4-yl]-amide | 2-(4-cyclopentyl-piperazin-1-yl)-pyridin-4-ylamine (intemediate 5) and 4-trifluoromethyl-piperidine | 426.3 |
| 69 | 411.59 | octahydro-quinoline-1-carboxylic acid [2-(4-cyclopentyl-piperazin-1-yl)-pyridin-4-yl]-amide | 2-(4-cyclopentyl-piperazin-1-yl)-pyridin-4-ylamine (intemediate 5) and decahydro-quinoline | 412.5 |
| 70 | 411.59 | octahydro-isoquinoline-2-carboxylic acid [2-(4-cyclopentyl-piperazin-1-yl)-pyridin-4-yl]-amide | 2-(4-cyclopentyl-piperazin-1-yl)-pyridin-4-ylamine (intemediate 5) and decahydro-isoquinoline | 412.5 |
| 71 | 405.55 | 3,4-dihydro-2H-quinoline-1-carboxylic acid [2-(4-cyclopentyl-piperazin-1-yl)-pyridin-4-yl]-amide | 2-(4-cyclopentyl-piperazin-1-yl)-pyridin-4-ylamine (intemediate 5) and 1,2,3,4-tetrahydro-quinoline | 406.4 |
| 72 | 405.55 | 3,4-dihydro-1H-isoquinoline-2-carboxylic acid [2-(4-cyclopentyl-piperazin-1-yl)-pyridin-4-yl]-amide | 2-(4-cyclopentyl-piperazin-1-yl)-pyridin-4-ylamine (intemediate 5) and 1,2,3,4-tetrahydro-isoquinoline | 406.4 |
| 73 | 357.5 | 2-methyl-pyrrolidine-1-carboxylic acid [2-(4-cyclopentyl-piperazin-1-yl)-pyridin-4-yl]-amide | 2-(4-cyclopentyl-piperazin-1-yl)-pyridin-4-ylamine (intemediate 5) and 2-methyl-pyrrolidine | 358.5 |
| 74 | 411.47 | 2-trifluoromethyl-pyrrolidine-1-carboxylic acid [2-(4-cyclopentyl-piperazin-1-yl)-pyridin-4-yl]-amide | 2-(4-cyclopentyl-piperazin-1-yl)-pyridin-4-ylamine (intemediate 5) and 2-trifluoromethyl-pyrrolidine | 412.4 |
| 75 | 385.56 | 2-isopropyl-pyrrolidine-1-carboxylic acid [2-(4-cyclopentyl-piperazin-1-yl)-pyridin-4-yl]-amide | 2-(4-cyclopentyl-piperazin-1-yl)-pyridin-4-ylamine (intemediate 5) and 2-isopropyl-pyrrolidine | 386.4 |
| 76 | 391.52 | 1,3-dihydro-isoindole-2-carboxylic acid [2-(4-cyclopentyl-piperazin-1-yl)-pyridin-4-yl]-amide | 2-(4-cyclopentyl-piperazin-1-yl)-pyridin-4-ylamine (intemediate 5) and 2,3-Dihydro-1H-isoindole | 392.3 |
| 77 | 391.52 | 2,3-dihydro-indole-1-carboxylic acid [2-(4-cyclopentyl-piperazin-1-yl)-pyridin-4-yl]-amide | 2-(4-cyclopentyl-piperazin-1-yl)-pyridin-4-ylamine (intemediate 5) and 2,3-dihydro-1H-indole | 392.2 |
| 78 | 389.54 | 3-[2-(4-cyclopentyl-piperazin-1-yl)-pyridin-4-yl]-1-isopropyl-1-(2-methoxy-ethyl)-urea | 2-(4-cyclopentyl-piperazin-1-yl)-pyridin-4-ylamine (intemediate 5) and isopropyl-(2-methoxy-ethyl)-amine | 390.4 |
| 79 | 371.53 | azepane-1-carboxylic acid [2-(4-cyclopentyl-piperazin-1-yl)-pyridin-4-yl]-amide | 2-(4-cyclopentyl-piperazin-1-yl)-pyridin-4-ylamine (intemediate 5) and azepane | 372.3 |
| 80 | 393.53 | 3-[2-(4-cyclopentyl-piperazin-1-yl)-pyridin-4-yl]-1-ethyl-1-phenyl-urea | 2-(4-cyclopentyl-piperazin-1-yl)-pyridin-4-ylamine (intemediate 5) and ethyl-phenyl-amine | 394.4 |
| 81 | 409.53 | 3-[2-(4-cyclopentyl-piperazin-1-yl)-pyridin-4-yl]-1-(4-methoxy-phenyl)-1-methyl-urea | 2-(4-cyclopentyl-piperazin-1-yl)-pyridin-4-ylamine (intemediate 5) and (4-methoxy-phenyl)-methyl-amine | 410.4 |

Intermediate 9

2-(4-Isopropyl-piperazin-1-yl)-pyridin-4-ylamine

Step 1: N-[2-(4-Isopropyl-piperazin-1-yl)-pyridin-4-yl]-acetamide

A mixture of 4.6 g (27 mmol) N-(2-chloropyridin-4-yl) acetamide (commercially available) and 5.2 g (41 mmol) 1-(2-propyl-)-piperazine in 2 ml DMF was heated to 150° C. for 4 h. Purification of the crude mixture with flash column chromatography on silica eluting with a gradient formed from DCM (1% NEt$_3$) and methanol yielded after evaporation of the product fractions 3.38 g (47%) of the title compound as white solid. MS: (m/e): 263.4 (MH$^+$).

Step 2: 2-(4-Isopropyl-piperazin-1-yl)-pyridin-4-ylamine

A mixture of 2.1 g (8 mmol) N-[2-(4-isopropyl-piperazin-1-yl)-pyridin-4-yl]-acetamide and 10.5 ml 4N HCl in 25 ml dioxane was heated to 100° C. for 2 h. After evaporation of all volatiles the residue was treated with water and NaHCO$_3$ aq. sat. and extracted with DCM. The combined organic layers were washed with NaCl aq. sat., dried with MgSO$_4$ and evaporated. The residue was triturated with DCM and dried to yield 1 g (57%) of the title compounds as white solid. MS: (m/e): 221.3 (MH$^+$).

Example 82

Cyclohexanecarboxylic acid [2-(4-isopropyl-piperazin-1-yl)-pyridin-4-yl]-amide

According to the procedure described for the synthesis of Example 1 the title compound was synthesized from 2-(4-isopropyl-piperazin-1-yl)-pyridin-4-ylamine (intermediate 9) and cyclohexanecarbonyl chloride (commercially available). MS: (m/e): 331.1 (MH$^+$).

Example 82

Methyl-cyclohexanecarboxylic acid [2-(4-isopropyl-piperazin-1-yl)-pyridin-4-yl]-amide According to the procedure described for the synthesis of Example 1 the title compound was synthesized from 2-(4-isopropyl-piperazin-1-yl)-pyridin-4-ylamine (intermediate 9) and 3-methyl-cyclohexanecarbonyl chloride (commercially available). MS: (m/e): 345.2 (MH$^+$).

Intermediate 10

[2-(4-Cyclopentyl-piperazin-1-yl)-pyridin-4-yl]-methyl-amine hydrochloride

Step 1: N-(2-Chloro-pyridin-4-yl)-N-methyl-acetamide

A mixture of 10 g (59 mmol) N-(2-chloropyridin-4-yl) acetamide (commercially available), 9.8 g (17.6 mmol) pulverized KOH and 4.1 ml (6.4 mmol) methyl iodide in 60 ml acetone was stirred at room temperature for 2 h. After evaporation of all volatiles the residue was taken up in water and extracted with ethyl acetate. The combined organic layers were dried with MgSO$_4$ and evaporated to yield 7.1 g (66%) of the title compound as off-white solid. MS: (m/e): 345.2 (MH$^+$).

Step 2: N-[2-(4-Cyclopentyl-piperazin-1-yl)-pyridin-4-yl]-N-methyl-acetamide

A mixture of 4 g (22 mmol) N-(2-chloro-pyridin-4-yl)-N-methyl-acetamide and 3.5 g (23 mmol) 1-(cyclopentyl)-piperazine was heated to 120° C. for 24 h. The crude product was purified by flash column chromatography on silica eluting with a gradient formed from heptane and ethyl acetate (0.1% NEt$_3$) to yield after evaporation of the product fractions 3.3 g (50%) of the title compound as light brow oil. MS: (m/e): 303.3 (MH$^+$).

Step 3: [2-(4-Cyclopentyl-piperazin-1-yl)-pyridin-4-yl]-methyl-amine hydrochloride A mixture of 3.3 g (11 mmol) N-[2-(4-cyclopentyl-piperazin-1-yl)-pyridin-4-yl]-N-methyl-acetamide and 12 ml 4N HCl in 5 ml water and 25 ml dioxane was stirred at room temperature. After evaporation of the volatiles the residue was triturated with a mixture formed from acetone and dioxane and dried under vacuum to yield 2.3 g (72%) of the title compound (intermediate 10) as off-white solid. MS: (m/e): 261.2 (MH$^+$).

Example 84

Cyclopentanecarboxylic acid [2-(4-cyclopentyl-piperazin-1-yl)-pyridin-4-yl]-methyl-amide According to the procedure described for the synthesis of Example 1 the title compound was synthesized from [2-(4-cyclopentyl-piperazin-1-yl)-pyridin-4-yl]-methyl-amine; hydrochloride (intermediate 10) and cyclopentanecarbonyl chloride (commercially available). MS: (m/e): 357.1 (MH$^+$).

Example 85

Methyl-cyclohexanecarboxylic acid [2-(4-cyclopentyl-piperazin-1-yl)-pyridin-4-yl]-methyl-amide According to the procedure described for the synthesis of Example 1 the title compound was synthesized from [2-(4-cyclopentyl-piperazin-1-yl)-pyridin-4-yl]-methyl-amine; hydrochloride (intermediate 10) and 3-methyl-cyclohexanecarbonyl chloride (commercially available). MS: (m/e): 385.2 (MH$^+$).

Example 86

Cyclohexanecarboxylic acid [2-(4-cyclopentyl-piperazin-1-yl)-pyridin-4-yl]-methyl-amide According to the procedure described for the synthesis of Example 1 the title compound was synthesized from [2-(4-cyclopentyl-piperazin-1-yl)-pyridin-4-yl]-methyl-amine hydrochloride (intermediate 10) and cyclohexanecarbonyl chloride (commercially available). MS: (m/e): 371.2 (MH$^+$).

Intermediate 11

[2-(4-Isopropyl-piperazin-1-yl)-pyridin-4-yl]-methyl-amine hydrochloride

Step 1: N-[2-(4-Isopropyl-piperazin-1-yl)-pyridin-4-yl]-N-methyl-acetamide

A mixture of 4 g (22 mmol) N-(2-chloro-pyridin-4-yl)-N-methyl-acetamide and 2.8 g (22 mmol) 1-(2-propyl)-piperazine was heated to 120° C. for 24 h. The crude product was purified by flash column chromatography on silica eluting with a gradient formed from heptane and ethyl acetate (0.1% NEt$_3$) to yield after evaporation of the product fractions 2.5 g (41%) of the title compound as light brow oil. MS: (m/e): 277.2 (MH$^+$).

Step 2: [2-(4-Isopropyl-piperazin-1-yl)-pyridin-4-yl]-methyl-amine hydrochloride A mixture of 2.5 g (9 mmol) N-[2-(4-isopropyl-piperazin-1-yl)-pyridin-4-yl]-N-methyl-acetamide and 10 ml 4N HCl in 5 ml water and 25 ml dioxane was stirred at room temperature. After evaporation of the volatiles the residue was triturated with a mixture formed from acetone and dioxane and dried under vacuum to yield 1.8 g (76%) of the title compound (intermediate 11) as light red solid. MS: (m/e): 235.2 (MH$^+$).

Example 87

Methyl-cyclohexanecarboxylic acid [2-(4-isopropyl-piperazin-1-yl)-pyridin-4-yl]-methyl-amide According to the procedure described for the synthesis of Example 1 the title compound was synthesized from [2-(4-isopropyl-piperazin-1-yl)-pyridin-4-yl]-methyl-amine hydrochloride (intermediate 11) and 3-methyl-cyclohexanecarbonyl chloride (commercially available). MS: (m/e): 359.2 (MH$^+$).

Example 88

Cyclohexanecarboxylic acid [2-(4-isopropyl-piperazin-1-yl)-pyridin-4-yl]-methyl-amide According to the procedure described for the synthesis of Example 1 the title compound was synthesized from [2-(4-isopropyl-piperazin-1-yl)-pyridin-4-yl]-methyl-amine hydrochloride (intermediate 11) and cyclohexanecarbonyl chloride (commercially available). MS: (m/e): 345.1 (MH$^+$).

Example 89

Piperidine-1-carboxylic acid [2-(4-cyclopentyl-piperazin-1-yl)-pyridin-4-yl]-methyl-amide A mixture of 20 mg (0.08 mmol) [2-(4-cyclopentyl-piperazin-1-yl)-pyridin-4-yl]-methyl-amine hydrochloride (intermediate 10), 46 mg (0.08 mmol) diphosgene and 31 mg (0.3 mmol) NEt$_3$ in 1 ml THF was treated with 43 mg (0.5 mmol) piperidine (commercially available) and stirred for 30 min at room temperature. After evaporation of all volatiles the residue was taken up in methanol/DMF and subjected to preparative HPLC purification on reversed phase eluting with a gradient of acetonitrile/water (0.05% triethylamine). The combined product fractions were evaporated to dryness to yield 15 mg (52%) of the title compound as white solid. MS (m/e): 372.1 (MH$^+$; 100%).

Example 90

Pyrrolidine-1-carboxylic acid [2-(4-cyclopentyl-piperazin-1-yl)-pyridin-4-yl]-methyl-amide According to the procedure described for the synthesis of Example 89 the title compound was synthesized from [2-(4-cyclopentyl-piperazin-1-yl)-pyridin-4-yl]-methyl-amine hydrochloride (intermediate 10), diphosgene and pyrrolidine (commercially available). MS (m/e): 358.0 (MH$^+$; 100%).

Example 91

4,4-Difluoro-piperidine-1-carboxylic acid [2-(4-cyclopentyl-piperazin-1-yl)-pyridin-4-yl]-methyl-amide According to the procedure described for the synthesis of Example 89 the title compound was synthesized from [2-(4-cyclopentyl-piperazin-1-yl)-pyridin-4-yl]-methyl-amine hydrochloride (intermediate 10), diphosgene and 4,4-difluoro-piperidine (commercially available). MS (m/e): 408.3 (MH$^+$; 100%).

Example 92

Cyclohexyl-1-[2-(4-cyclopentyl-piperazin-1-yl)-pyridin-4-yl]-1-methyl-urea

According to the procedure described for the synthesis of Example 1 the title compound was synthesized from [2-(4-cyclopentyl-piperazin-1-yl)-pyridin-4-yl]-methyl-amine hydrochloride (intermediate 10) and isocyanato-cyclohexane (commercially available). MS: (m/e): 386.4 (MH$^+$).

Example 93

Cyclopentyl-1-[2-(4-cyclopentyl-piperazin-1-yl)-pyridin-4-yl]-1-methyl-urea

According to the procedure described for the synthesis of Example 1 the title compound was synthesized from [2-(4-cyclopentyl-piperazin-1-yl)-pyridin-4-yl]-methyl-amine hydrochloride (intermediate 10) and isocyanato-cyclopentane (commercially available). MS: (m/e): 372.3 (MH$^+$).

Example 94

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example 95

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 96

Injection solutions can have the following composition:

| Compound of formula (I) | 3.0 mg |
|---|---|
| Gelatine | 150.0 mg |
| Phenol | 4.7 mg |
| Sodium carbonate | to obtain a final pH of 7 |
| Water for injection solutions | ad 1.0 ml |

Example 97

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to procedures typically used in the art.

Example 98

Sachets containing the following ingredients can be manufactured in a conventional manner:

| Compound of formula (I) | 50.0 mg |
|---|---|
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and flavoring additives and filled into sachets.

It is to be understood that the invention is not limited to the particular embodiments of the invention described above, as variations of the particular embodiments may be made and still fall within the scope of the appended claims.

What is claimed is:

1. A compound of the formula I:

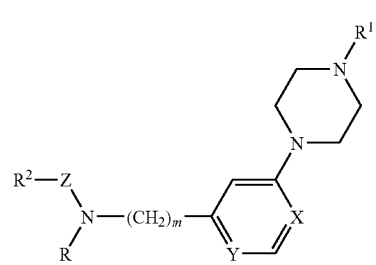

wherein:
R is hydrogen or lower alkyl;
$R^1$ is selected from the group consisting of hydrogen, lower alkyl, $C_3$-$C_7$-alkenyl, $C_3$-$C_7$-alkinyl, lower halogenalkyl, lower hydroxyalkyl, lower alkoxyalkyl, $C_3$-$C_7$-cycloalkyl and lower $C_3$-$C_7$-cycloalkylalkyl;
X is N and Y is C, or
Y is N and X is C;
m is 1;
Z is $SO_2$;
$R^2$ is selected from the group consisting of lower alkyl, $C_3$-$C_7$-alkenyl, $C_3$-$C_7$-alkinyl, lower halogenalkyl, lower hydroxyalkyl, lower alkoxyalkyl,
$C_3$-$C_7$-cycloalkyl or $C_3$-$C_7$-cycloalkyl substituted by phenyl or lower alkyl,
lower $C_3$-$C_7$-cycloalkylalkyl,
unsubstituted phenyl or phenyl mono- or disubstituted by lower alkoxy or lower halogenalkyl, lower phenylalkyl wherein the phenyl ring is unsubstituted or mono- or disubstituted by lower alkyl, lower alkoxy, halogen or lower halogenalkyl,
unsubstituted pyridyl or pyridyl mono- or disubstituted by lower alkoxy or halogen, and —$NR^3R^4$,
$R^3$ is hydrogen or lower alkyl;
$R^4$ is selected from the group consisting of
lower alkyl, $C_3$-$C_7$-alkenyl, $C_3$-$C_7$-alkinyl,
lower alkoxyalkyl,
$C_3$-$C_7$-cycloalkyl, $C_3$-$C_7$-cycloalkyl substituted by phenyl, lower $C_3$-$C_7$-cycloalkylalkyl,
unsubstituted phenyl or phenyl mono- or disubstituted by lower alkyl, lower alkoxy, halogen or lower halogenalkyl, or
lower phenylalkyl wherein phenyl is unsubstituted or mono- or disubstituted by lower alkyl, lower alkoxy, halogen or lower halogenalkyl; or R³ and R⁴ together with the nitrogen atom to which they are attached form a 4-, 5-, 6- or 7-membered heterocyclic ring optionally containing a further heteroatom selected from nitrogen, oxygen or sulfur, said heterocyclic ring being unsubstituted or substituted by one, two or three groups independently selected from lower alkyl, lower alkoxy, oxo, halogen and halogenalkyl, or being condensed with a phenyl or cyclohexyl ring, said phenyl or cyclohexyl ring being unsubstituted or substituted by one, two or three groups independently selected from lower alkyl, lower alkoxy, halogen and halogenalkyl;

and pharmaceutically acceptable salts thereof.

2. The compound according to claim 1, wherein R¹ is lower alkyl or C₃-C₇-cycloalkyl.

3. The compound according to claim 1, wherein R¹ is C₃-C₇-cycloalkyl.

4. The compound according to claim 1, wherein R¹ is ethyl or isopropyl.

5. The compound according to claim 1, wherein R is hydrogen and R² is selected from the group consisting of lower alkyl, C₃-C₇-alkenyl, C₃-C₇-alkinyl, lower halogenalkyl, lower hydroxyalkyl, lower alkoxyalkyl, C₃-C₇-cycloalkyl or C₃-C₇-cycloalkyl substituted by phenyl, lower C₃-C₇-cycloalkylalkyl, unsubstituted phenyl or phenyl mono- or disubstituted by lower alkoxy or lower halogenalkyl, lower phenylalkyl wherein the phenyl ring is unsubstituted or mono- or disubstituted by lower alkyl, lower alkoxy, halogen or lower halogenalkyl, unsubstituted pyridyl or pyridyl mono- or disubstituted by lower alkoxy or halogen, and —NR³R⁴.

6. The compound according to claim 1, wherein R² is selected from the group consisting of lower alkyl, C₃-C₇-alkenyl, C₃-C₇-alkinyl, lower halogenalkyl, lower hydroxyalkyl, lower alkoxyalkyl, C₃-C₇-cycloalkyl or C₃-C₇-cycloalkyl substituted by phenyl or lower alkyl, lower C₃-C₇-cycloalkylalkyl, lower phenylalkyl wherein the phenyl ring is unsubstituted or mono- or disubstituted by lower alkyl, lower alkoxy, halogen or lower halogenalkyl, unsubstituted pyridyl or pyridyl mono- or disubstituted by lower alkoxy or halogen, and —NR³R⁴.

7. The compound according to claim 1, wherein R² is selected from the group consisting of lower alkyl, C₃-C₇-cycloalkyl and lower alkoxyalkyl.

8. The compound according to claim 1, wherein R² is lower phenylalkyl wherein phenyl is unsubstituted or mono- or disubstituted by lower alkyl, lower alkoxy, halogen or lower halogenalkyl.

9. The compound according to claim 1, wherein R² is —NR³R⁴ and R³ and R⁴ are as defined in claim 1.

10. The compound according to claim 1, wherein R³ and R⁴ are lower alkyl.

11. The compound according to claim 9, wherein R³ is hydrogen or lower alkyl and R⁴ is selected from the group consisting of lower alkyl, C₃-C₇-alkenyl, C₃-C₇-alkinyl, lower alkoxyalkyl, C₃-C₇-cycloalkyl, C₃-C₇-cycloalkyl substituted by phenyl, lower C₃-C₇-cycloalkylalkyl, unsubstituted phenyl or phenyl mono- or disubstituted by lower alkyl, lower alkoxy, halogen or lower halogenalkyl, and lower phenylalkyl wherein phenyl is unsubstituted or mono- or disubstituted by lower alkyl, lower alkoxy, halogen or lower halogenalkyl.

12. The compound according to claim 9, wherein R³ and R⁴ together with the nitrogen atom to which they are attached form a 4-, 5-, 6- or 7-membered heterocyclic ring optionally containing a further heteroatom selected from nitrogen, oxygen or sulfur, said heterocyclic ring being unsubstituted or substituted by one, two or three groups independently selected from lower alkyl, lower alkoxy, oxo, halogen and halogenalkyl, or being condensed with a phenyl or cyclohexyl ring, said phenyl or cyclohexyl ring being unsubstituted or substituted by one, two or three groups independently selected from lower alkyl, lower alkoxy, halogen and halogenalkyl.

13. The compound according to claim 1, wherein R² is unsubstituted phenyl or phenyl mono- or disubstituted by lower alkoxy or lower halogenalkyl.

14. The compound according to claim 1, wherein X is N and Y is C.

15. The compound according to claim 1, wherein X is C and Y is N.

16. The compound according to claim 1, wherein R is hydrogen.

17. The compound according to claim 1, wherein R is methyl.

18. The compound according to claim 1, selected from the group consisting of

N-[2-(4-ethyl-piperazin-1-yl)-pyridin-4-yl]-C-phenyl-methanesulfonamide,

C-(4-chloro-phenyl)-N-[2-(4-ethyl-piperazin-1-yl)-pyridin-4-yl]-methanesulfonamide, C-(4-chloro-phenyl)-N-[2-(4-cyclopentyl-piperazin-1-yl)-pyridin-4-yl]-methanesulfonamide, propane-1-sulfonic acid [2-(4-cyclopentyl-piperazin-1-yl)-pyridin-4-ylmethyl]-amide, dimethylamine-1-sulfonic acid [2-(4-cyclopentyl-piperazin-1-yl)-pyridin-4-ylmethyl]-amide, C-(4-chloro-phenyl)-N-[2-(4-cyclopentyl-piperazin-1-yl)-pyridin-4-ylmethyl]-methanesulfonamide, and N-[2-(4-cyclopentyl-piperazin-1-yl)-pyridin-4-ylmethyl]-benzenesulfonamide, and pharmaceutically acceptable salts thereof.

19. A process for the manufacture of a compound according to claim 1, comprising the steps of:

reacting a compound of the formula II

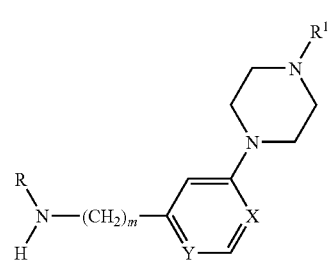

wherein X, Y, R, R¹ and m are as defined in claim 1, with a sulfonylchloride or sulfamoylchloride of the formula III $$R^2\text{—}SO_2\text{—}Cl \qquad \text{III}$$

wherein R² is as defined herein before,
to obtain a compound of the formula I-A

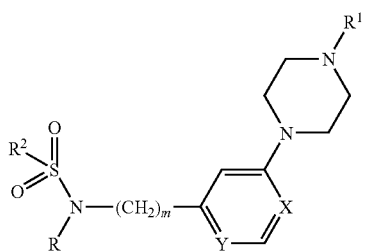

I-A wherein X, Y, R, R¹, R² and m are as defined in claim 1
and if desired, converting the compound of formula I-A into a pharmaceutically acceptable salt.

20. A pharmaceutical composition, comprising a therapeutically effective amount of a compound according to claim 1 and a pharmaceutically acceptable carrier and/or adjuvant.

21. A method for the treatment of obesity, comprising the step of administering a therapeutically effective amount of a compound according to claim 1 to a human being or animal in need thereof.

\* \* \* \* \*